United States Patent [19]
Dunfee

[11] Patent Number: 5,950,628
[45] Date of Patent: Sep. 14, 1999

[54] INFLATABLE WEARABLE TRACTION DEVICE

[75] Inventor: Matthew J. Dunfee, Jordan, Minn.

[73] Assignee: Kinesis Medical, Inc., Minneapolis, Minn.

[21] Appl. No.: 09/015,715

[22] Filed: Jan. 29, 1998

Related U.S. Application Data

[63] Continuation-in-part of application No. 08/580,708, Dec. 29, 1995, Pat. No. 5,724,993, which is a continuation-in-part of application No. 08/806,424, Feb. 26, 1997, Pat. No. 5,704,904
[60] Provisional application No. 60/036,995, Jan. 31, 1997.
[51] Int. Cl.$^6$ ........................................................ A61F 5/37
[52] U.S. Cl. ................................ 128/874; 602/13; 602/19
[58] Field of Search ................................... 128/845, 846, 128/882, DIG. 20; 602/5, 13, 19; 2/2

[56] References Cited

U.S. PATENT DOCUMENTS

| | | |
|---|---|---|
| 1,589,670 | 6/1926 | Vartia . |
| 3,186,405 | 6/1965 | Bailey et al. . |
| 3,521,623 | 7/1970 | Nichols et al. . |
| 3,823,712 | 7/1974 | Morel . |
| 3,868,952 | 3/1975 | Hatton . |
| 4,269,179 | 5/1981 | Burton et al. . |
| 4,497,517 | 2/1985 | Gmeiner et al. . |
| 4,552,135 | 11/1985 | Racz et al. . |
| 4,559,933 | 12/1985 | Batard et al. . |
| 4,567,887 | 2/1986 | Couch, Jr. . |
| 4,622,957 | 11/1986 | Curlee . |
| 4,685,668 | 8/1987 | Newlin, Jr. . |
| 4,691,696 | 9/1987 | Farfan de los Godos . |
| 4,702,235 | 10/1987 | Hong . |
| 4,768,499 | 9/1988 | Kemp . |
| 4,898,185 | 2/1990 | Fuller . |
| 4,960,115 | 10/1990 | Ranciato . |
| 4,991,572 | 2/1991 | Chases . |
| 4,991,573 | 2/1991 | Miller . |
| 5,060,639 | 10/1991 | Marcus . |
| 5,062,414 | 11/1991 | Grim . |
| 5,076,264 | 12/1991 | Lonardo et al. . |
| 5,101,815 | 4/1992 | Langdon-Orr et al. . |
| 5,111,807 | 5/1992 | Spahn et al. . |
| 5,135,471 | 8/1992 | Housewerth . |
| 5,188,586 | 2/1993 | Castel et al. . |
| 5,256,135 | 10/1993 | Avihod . |
| 5,338,289 | 8/1994 | Cooker . |
| 5,382,226 | 1/1995 | Graham . |
| 5,403,266 | 4/1995 | Bragg et al. . |
| 5,441,479 | 8/1995 | Chitwood . |

OTHER PUBLICATIONS

AliMed inc. Catalog, 1993, p. 28.
Flaghouse Rehab Catalog, Summer 1993, p. 30.
The Saunders Group, Inc., 1992 Catalog, p. 37.

*Primary Examiner*—Michael A. Brown
*Attorney, Agent, or Firm*—Patterson & Keough, P A.

[57] ABSTRACT

An ambulatory, wearable support to be worn by a person for applying an extending force to a portion of the human anatomy while being worn, the portion of the human anatomy having an anterior portion and an opposed posterior portion, includes a first anchor member substantially encircling a first portion of the human anatomy, A second anchor member is spaced apart from the first anchor member, the portion of the human anatomy that is to be subjected to the extending force being disposed substantially between said first and second anchor members. A plurality of extender sets have at least one selectively inflatable bladder. The at least one bladder has a first end operably coupled to the first anchor member and a second end operably coupled to the second anchor member, the plurality of extender sets being spaced apart and disposed both anteriorly and posteriorly with respect to the portion of the human anatomy that is to be subjected to the extending force. In preferred embodiments, the ambulatory, wearable support comprise a maternal support and a wrist support.

23 Claims, 12 Drawing Sheets

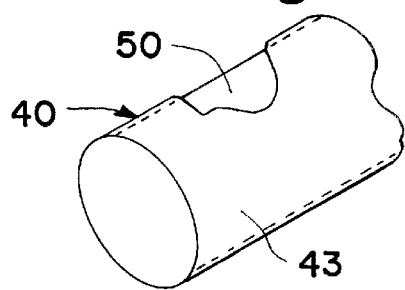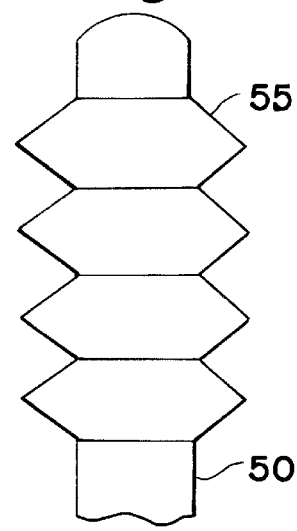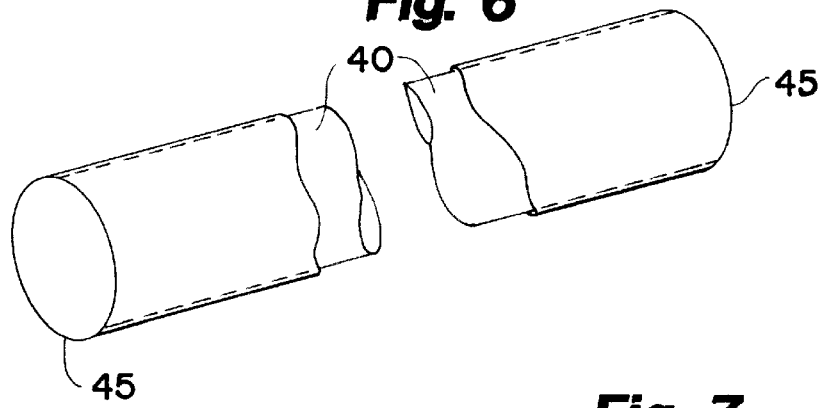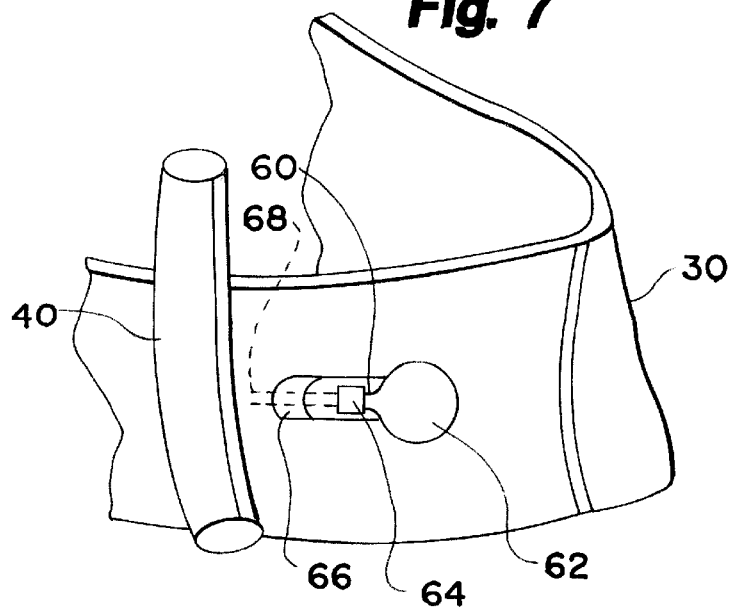

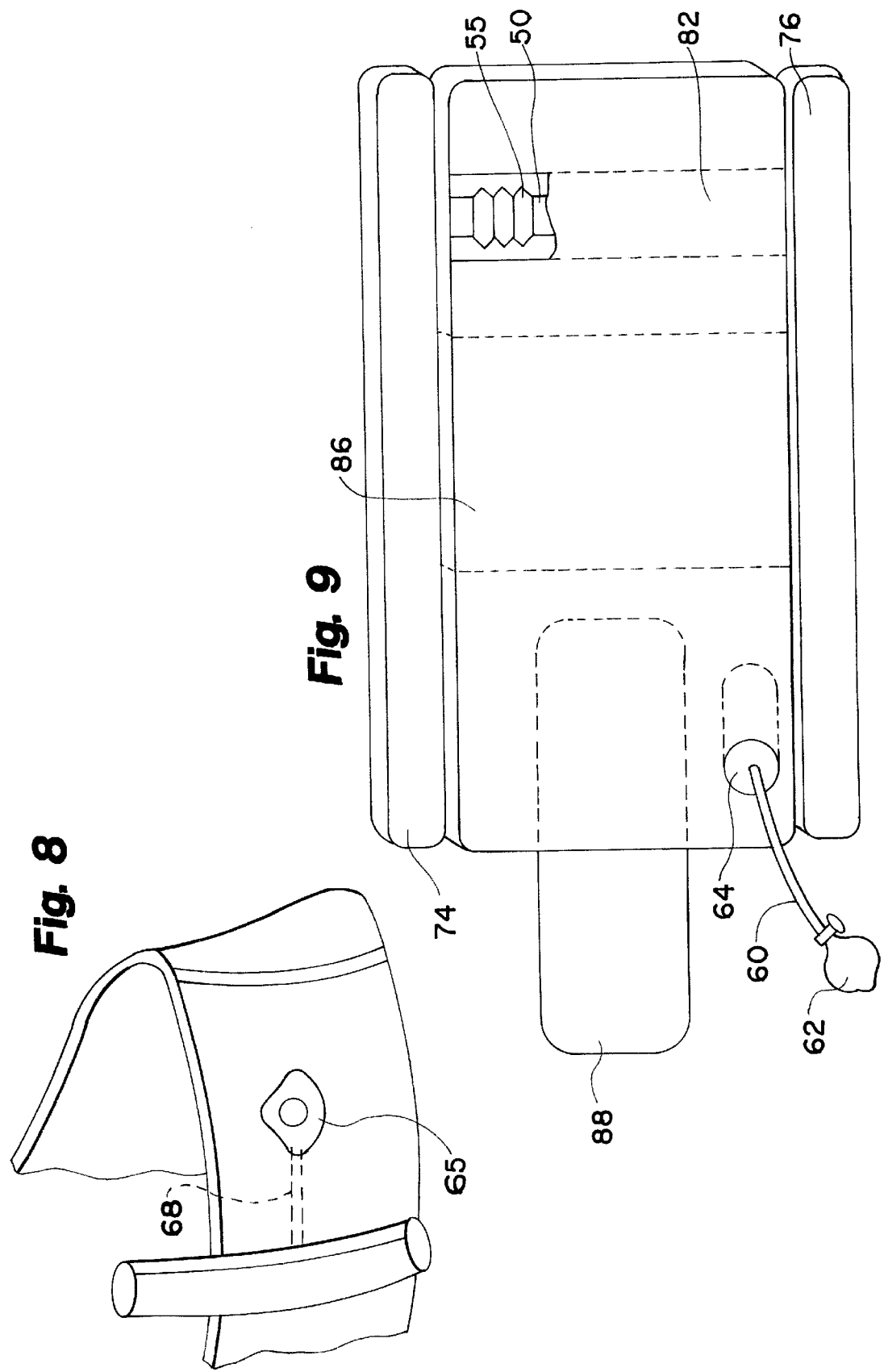

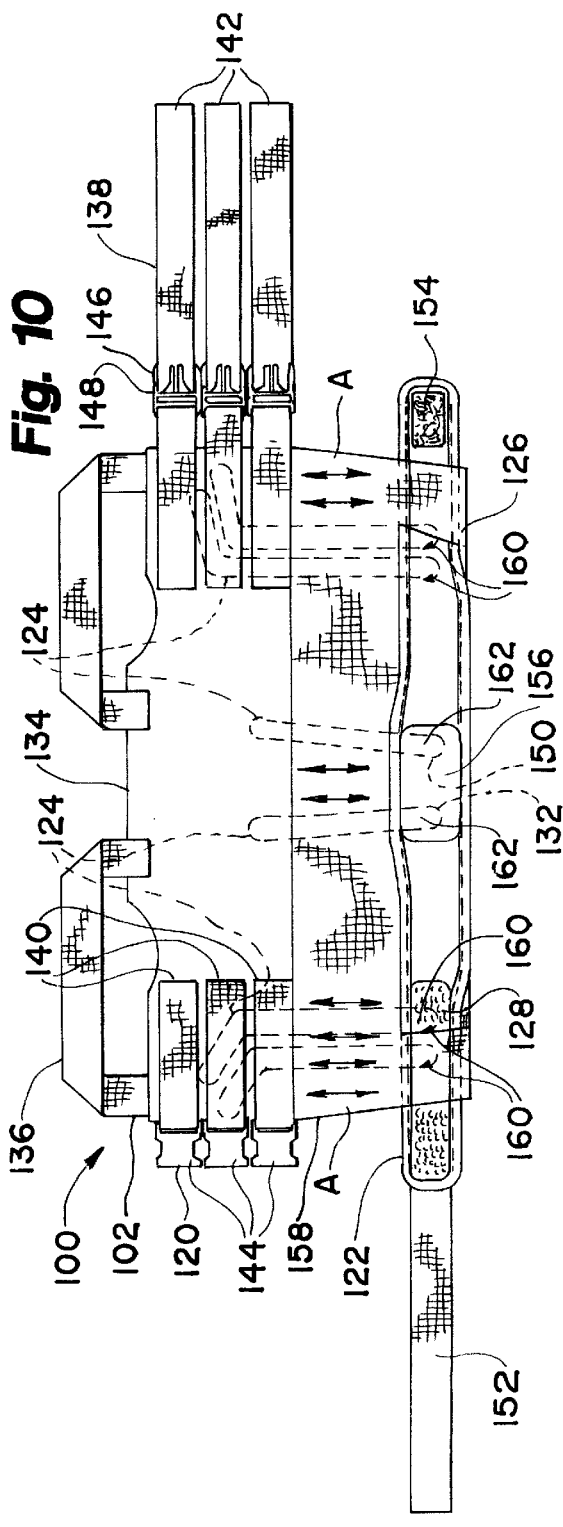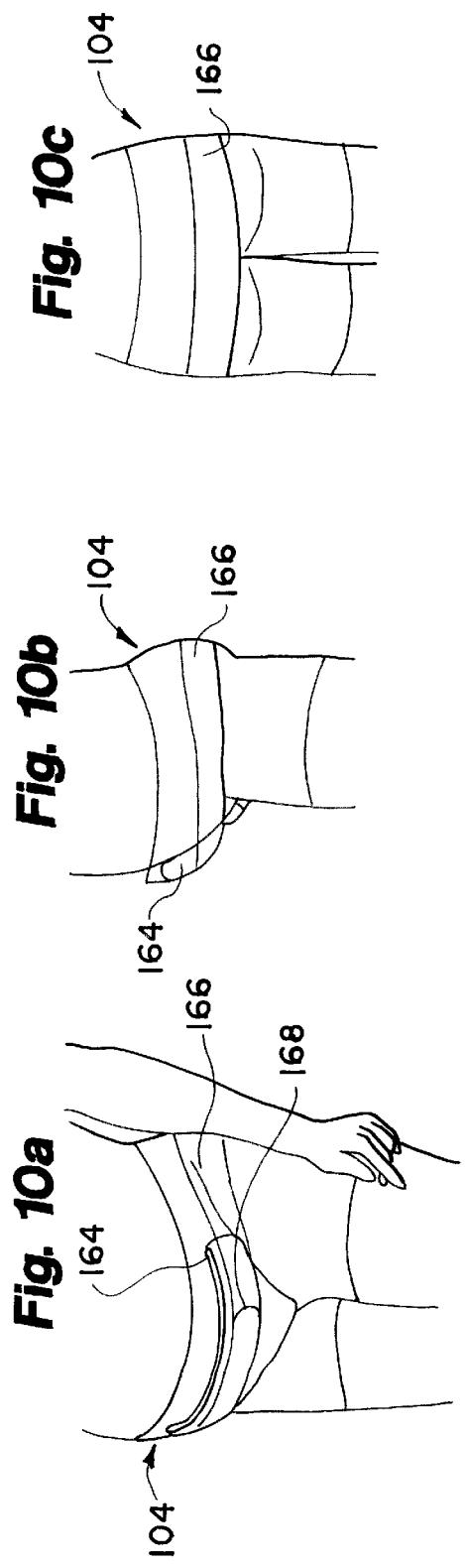

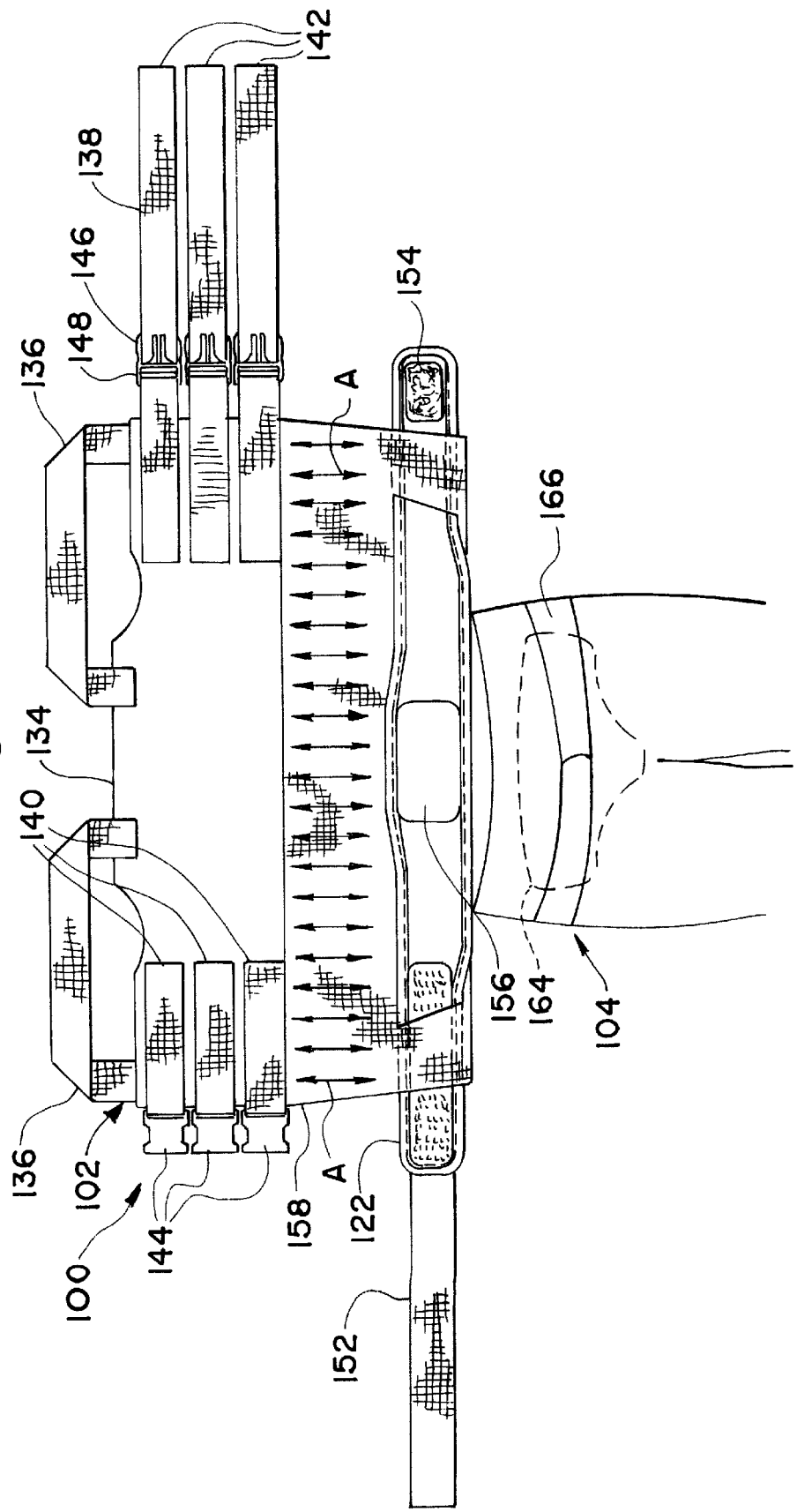

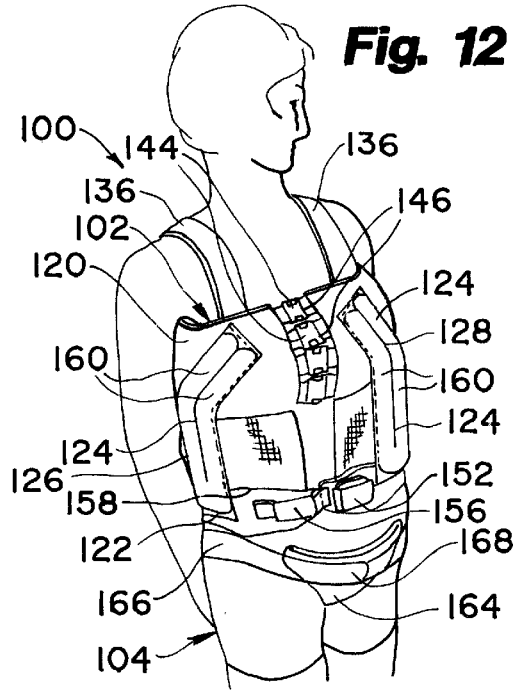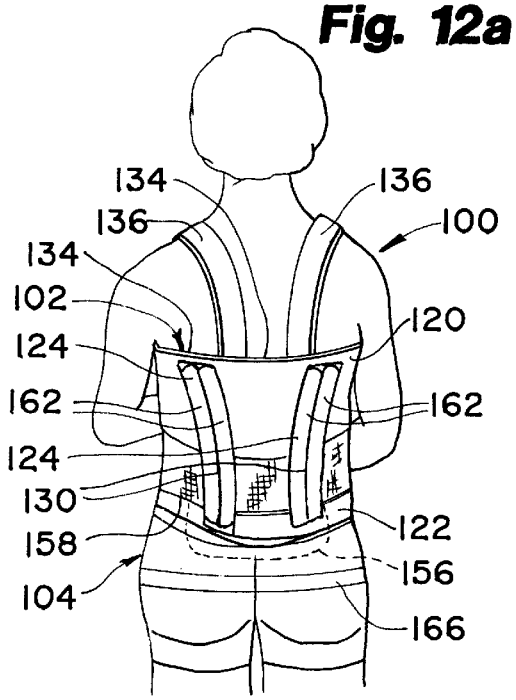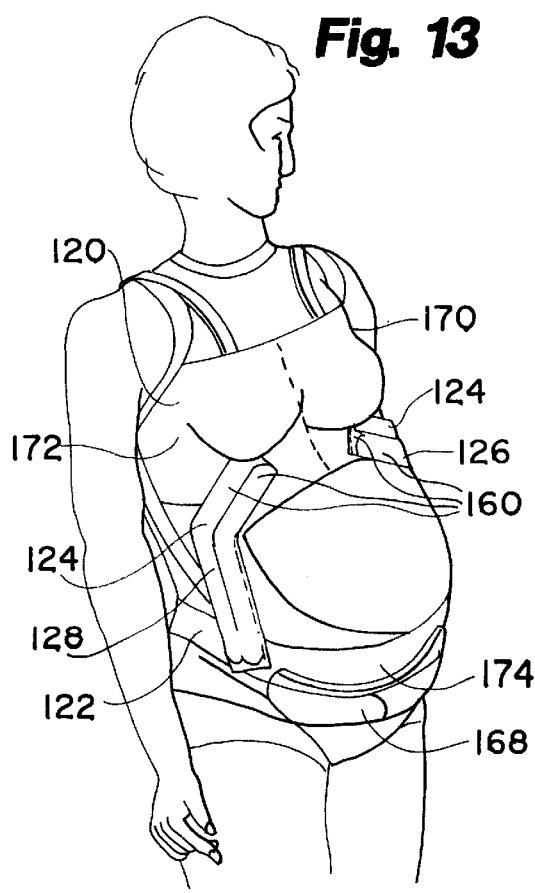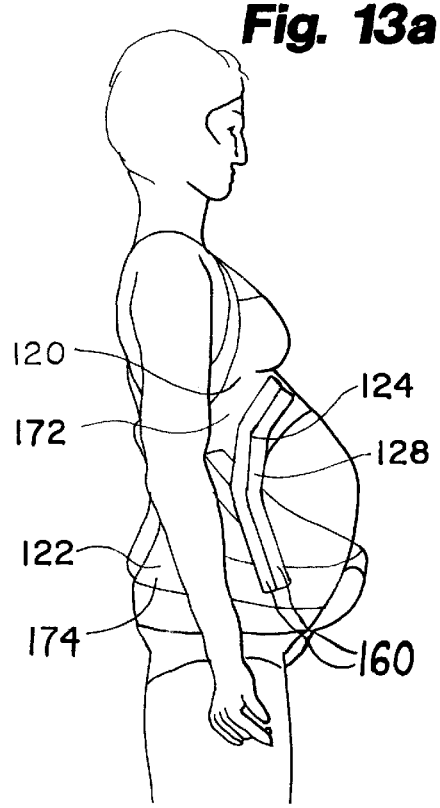

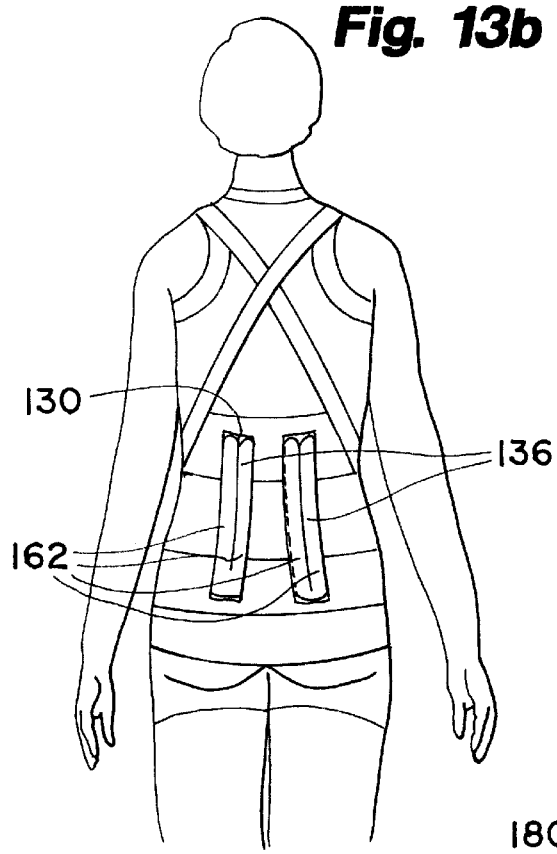
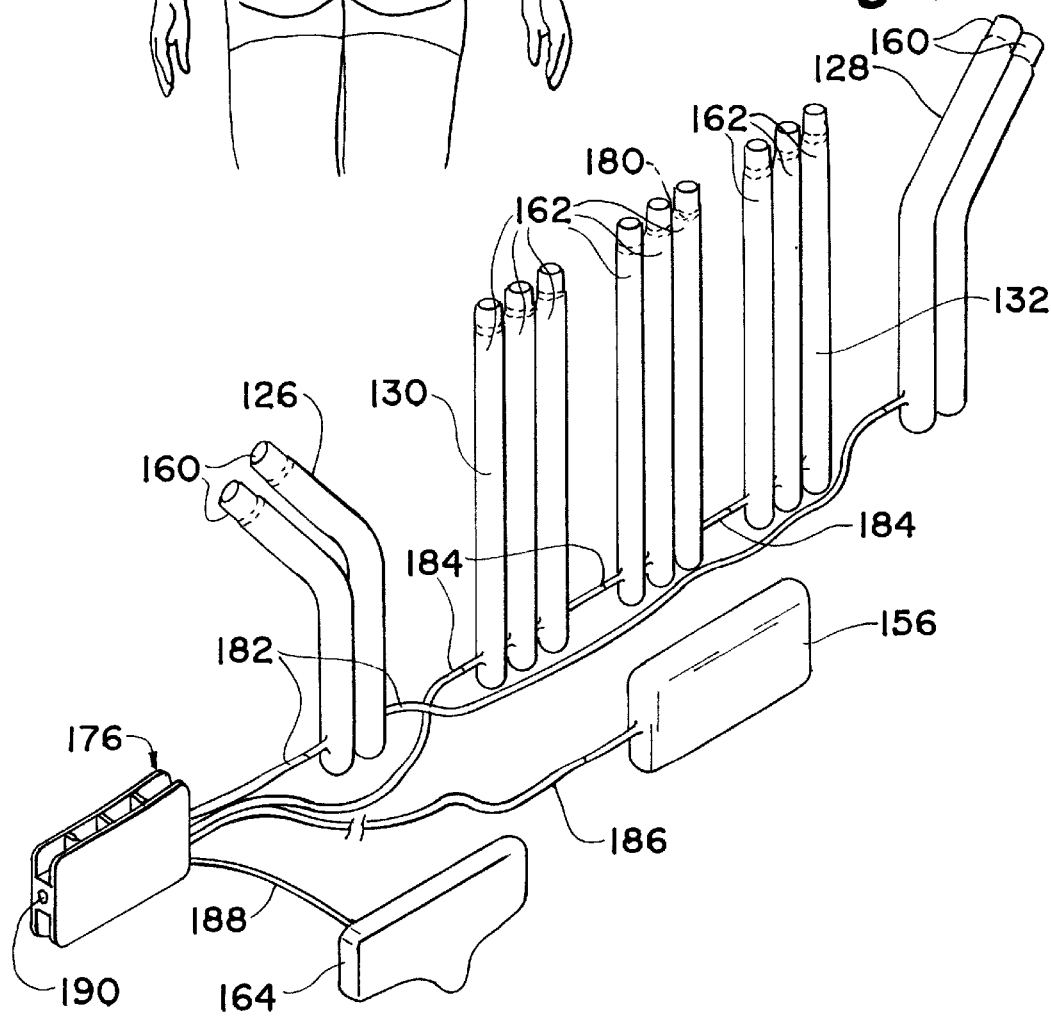

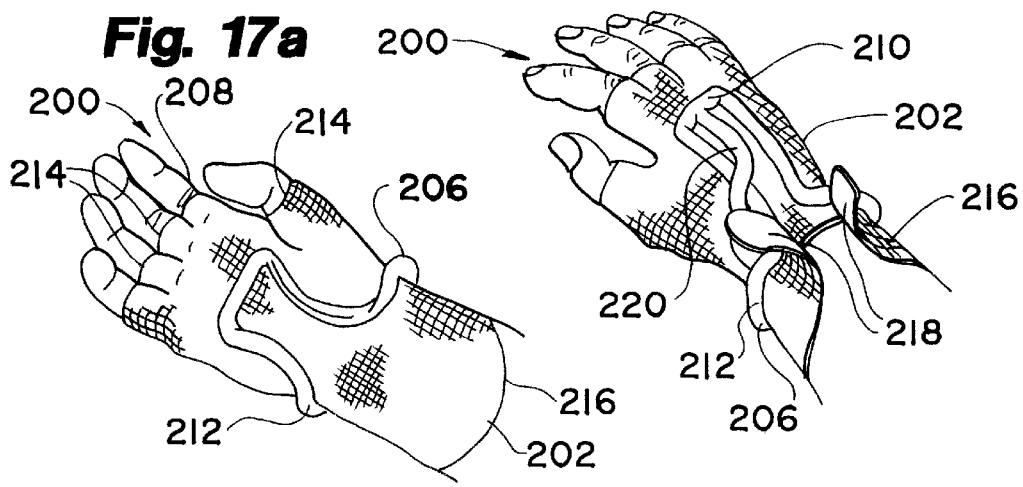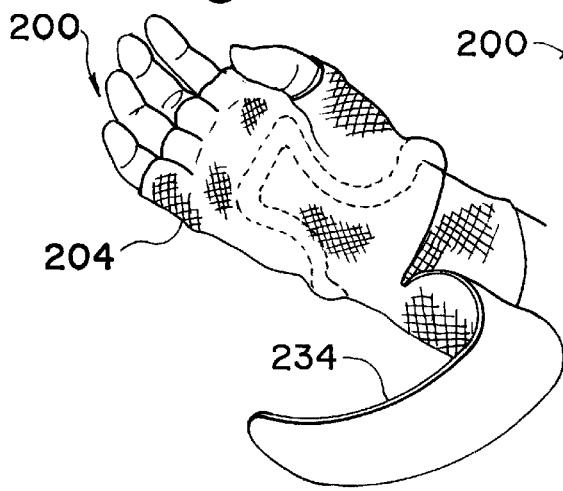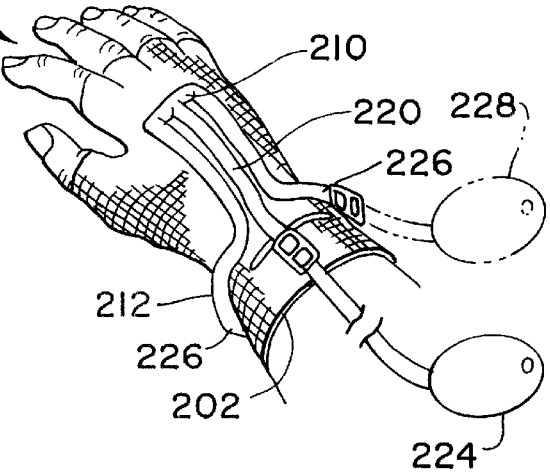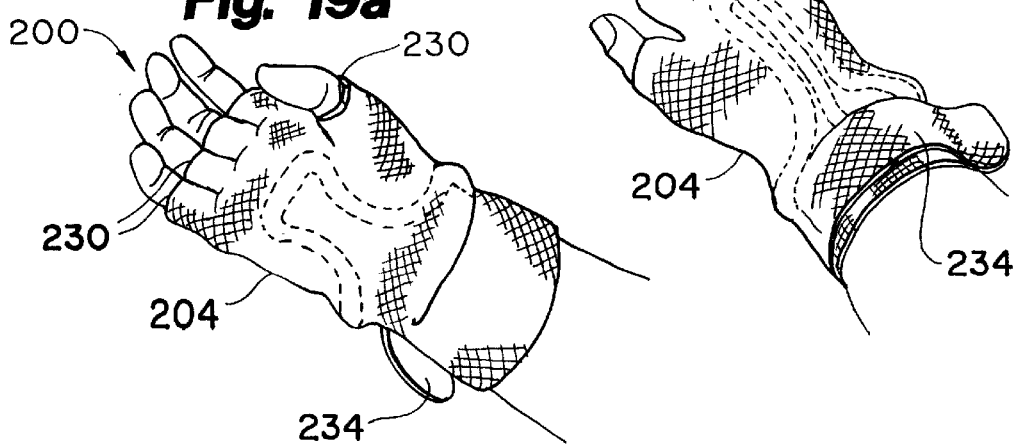

INFLATABLE WEARABLE TRACTION DEVICE

CROSS-REFERENCE TO RELATED APPLICATIONS

This is a continuation-in-part of U.S. application Ser. No. 08/580,708 filed Dec. 29, 1995 now U.S. Pat. No. 5,724,993, which is a continuation-in-part of U.S. application Ser. No. 08/806,424 filed Feb. 26, 1997, now issued as U.S. Pat. No. 5,704,904 on Jan. 6, 1998, and the present application claims the benefit of U.S. Provisional Application No. 60/036,995 filed Jan. 31, 1997.

FIELD OF THE INVENTION

This invention relates in general to maternal support devices to aid in the relieving of lower back pain, posterior pelvic pain, exaggerated lumbar curve, and support to the abdominal pelvic ring. This invention further relates in general to devices to aid in the healing of carpal tunnel injuries, arthritis or to support various wrist regions to prevent the occurrence or reoccurrence of injuries.

BACKGROUND OF THE INVENTION

Humans have long dealt with the pain, aggravation and loss of productivity arising from spinal injuries, particularly those to the lower back. It is not without good reason that the phrase, "Oh, my aching back!" is a common part of our everyday lexicon. The relative ease with which injuries to the spine and supporting musculature are incurred, as well as the debilitating effects of even slight injuries, merely adds to the overall severity of the problem of dealing with spinal injuries. Further aggravating the situation is that the most frequently prescribed regimen of treatment for spine-related injuries, short of surgical intervention, is the cessation or severe curtailment of almost all physical activities likely to give rise to torsional or compressional stresses to the affected regions of the spinal cord. In practical terms, due to the pervading effect of the spinal anatomy on all but the most sedentary and isolated of physical activities, almost complete immobility must be imposed to insure providing an injured spinal area sufficient opportunity to heal. In this context, the term "injury" relates not only to actual compression and torsional injuries to the various anatomical structures of the spinal cord and related neurophysiology, but also to general musculature strains of the large muscle groups interacting with various anatomical regions of the spinal cord.

The human spinal column is a major component of the skeletal system of thirty-three bones comprising seven cervical, twelve thoracic, and five lumbar vertebrae, with the latter merging endwardly into the five fused sacral and the four fused coccyx vertebrae. The twenty-four individual vertebrae have various bony projections with one projection, directed outward from the back of the spine, known as the spinous process. The individual vertebrae are connected and supported by various cartilages, muscles and ligaments which allow flexibility for bending and twisting of the torso. Between each vertebra is an intervertebral disc which functions to cushion and separate each vertebra, helping to prevent compression of the peripheral spinal nerves branching off from the spinal cord and housed within the spinal column. When subject to stresses, the interior structure of the disc can degenerate and/or rupture leading to a displacement of the intra-disc cushioning material and a resulting bulging of the outer disc surface. This bulging can impinge on nerve structures causing inflammation and aggravation of the neurological anatomy involved. Such neurological involvement is invariably accompanied by pain, loss of muscle strength decrease range of motion of the spine and possibly neurological involvement. In some cases, the outer surface of the disc can rupture completely leading to an extrusion of the viscous intra-disc material, a condition which can generally require invasive therapy.

Loss of normal spinal contour can also result in pain, in loss of motion, and neuro involvement.

A significant proportion of back pain experienced by the general public occurs in the lower portion of the back generally referred to as the lumbar region, or spinal segments L-1 through L-5. In those instances where pain is the result of neuro impingement, the pressure exerted against the nerves may be reduced by re-establishing normal contour of vertebrae of this region, resulting in reduction or elimination of pain. In a similar fashion, a proportion of spinal pain affecting the cervical region, or spinal segments C-1 through C-7, may be alleviated through reduction of neuro impingement at this level. A clinical approach to reduce this neuro impingement re-establish contour may involve use of traction. Traction has been demonstrated to be therapeutically effective in promoting healing of the affected anatomy with accompanying reduction of symptoms.

Back injuries are a very costly health problem for industry, as measured in terms of lost productivity. Some estimates place the total cost of back injuries to industry in the United States at approximately one hundred billion dollars per year. It is estimated that each year nearly half a million workers are permanently sidelined by back injuries. Lower back pain and other back injuries account for nearly forty percent of all work days missed, resulting in over 93 million lost work days per year. Many lower back injuries and low back pain result from improper lifting mechanics and technique. Thus, many of these injuries that occur could be prevented by proper lifting techniques; however, even with training in proper techniques, many workers fail to use such techniques and become injured.

The lumbar spine can be injured in many ways—two of which are namely, compression or torsion injuries. If the former occurs, a common result is damage to the vertebral endplate. Treatment option include: rest and physical therapy, medications and avoidance of physical activity likely to place excess stress on the spinal column. Surgery is rarely required, as is typical of the vast majority of day-to-day back injuries.

If torsion or twisting occurs, the common result is damage to the intervertebral disc. In some cases, the nucleus of an injured disc may rupture the annulus of the disc and protrude therethrough. Such a protrusion, or "slipped disc", can pinch the spinal nerves causing LBP and/or leg pain, muscle weakness and rarely paresis or paralysis. Corrective surgery to remove the protured disc material may be required. A series of minor torsional injuries may result in a weakened disc, which may be susceptible to more serious injury. Twisting toward an injured side may aggravate the injury and interfere with the healing process.

Because the human spine is the essential load bearing component in the human skeleton, an injury to any region of the spine generally causes some discomfort, immobility and/or pain. After an injury has occurred, it is important that the spine be given an opportunity to heal. Spinal motion around the injury should be avoided. If inadequate healing occurs, an injury may become chronic in nature, causing ongoing pain and discomfort to the affected individual. Because the spine is in constant use, it is continuously subjected to stresses which may interfere with the healing process. In some cases, bed rest, and other non-surgical measures may be adequate to allow an injury to heal fully.

Due to the frequency of spinal injuries, and the economic impact on the productivity and efficiency of both industrial workers and the general populace that result from such conditions, considerable attention has been directed toward the development of devices designed to address the problems associated with back and neck pain of varying etiologies. These devices can be characterized accordingly: First of all, there are many devices designed to prevent the occurrence of lower back injuries such as support belts and braces for workers engaged in repetitive lifting activities, or for the general populace during occasional lifting or athletic endeavors. Secondly, there are devices designed to be worn during everyday activities by individuals already exhibiting lumbar or cervical spinal injury symptoms. These devices can be similar in design to the preventative devices, allow the wearer to engage in activities while, in theory, still removing sufficient stress from the affected region of the spine to permit healing of the injury. Lastly, there is a group of devices designed to provide active therapeutic benefit in a clinical setting. Mechanical and/or gravitational traction devices for treating either the cervical or lumbar regions of the spine are exemplary of such devices.

With respect to the first class of devices mentioned above, it has been found that support to the lower back of workers through the use of belts, braces or wraps can reduce the occurrence of back injuries, perhaps because such devices provide support, and encourage workers to use better lifting technique. Such belts, braces or wraps appear to provide support by compressing the tissue around the spine so as to stabilize the lumbar region and prevent substantial lateral motion of the lumbar vertebrae relative to one another which, if left unconstrained, could otherwise occur and cause painful injury. Such devices are of little benefit, for a variety of practical reasons, for prevention of injuries to the cervical spine.

Many support belts used in the past were widened belts which were tightened to provide pressure, and did not promote correct extension of the spine. This type of device is exemplified by the U.S. Pat. No. 4,685,668, issued on a weight lifting belt to T. L. Newlin, Jr. on Aug. 11, 1987. These belts were relatively rigid and too much pressure could be applied directly on the spinous processes of the vertebrae, which was especially evident when the wearer bent over, resulting in pain along the spine. Wearing this type of belt for an extended period of time also tended to constrict blood flow and cause skin irritation.

Many of these prior art belts, braces or wraps have also been designed specifically to reinforce proper lifting techniques. When lifting heavy objects, it is preferable to use the legs as much as possible to perform the lift, thus relieving strain from the spine and muscles of the back. To insure that the legs are doing most of the lifting as opposed to the back, the lift should begin with the lifter in a squatting position with the back aligned within 45 degrees of vertical. However, individuals often lift items with the back aligned 45–90 degrees beyond vertical such that the back bears most of the load during lifting. Many braces incorporate features which make it uncomfortable for a wearer to bend their back more than 45 degrees from vertical, thereby mechanically constraining the wearer from exceeding a degree of alignment of the back associated with proper lifting technique.

Often these devices employ padded regions designed to come in contact with the lumbar region of the spine, providing additional support to that region. Specific examples of belts designed to place various pads against the lumbar region of the wearer's back are shown in U.S. Pat. No. 4,991,573 to Miller in which the principal inventive focus of the device is the specific design of the lumbar pad; U.S. Pat. No. 5,188,586 to Castel et al. which discloses a back brace designed to prevent injuries to the lower back and impose proper lifting technique on the wearer by constraining the range of motion during lifting; U.S. Pat. No. 4,768,499 to Kemp discloses a lifting belt with an unpadded lumbar panel, also designed to provide additional support to the abdominal region of the wearer during lifting; and U.S. Pat. No. 5,060,639 to Marcus which also discloses a back support providing additional support to the abdominal region of the wearer, including an embodiment suited for use by expectant mothers in the latter stages of pregnancy.

Numerous examples also exist of braces and belts which utilize a lumbar pad comprising fluid-filled compartments designed to conform to the unique contours of the wearer's back. For example, U.S. Pat. No. 4,622,957, issued Nov. 18, 1986 to Curlee, discloses a therapeutic corset adapted for the sacrum, lumbar and thoracic regions of the body. The corset includes a padded bladder provided with a duct for introducing fluid. The inflated bladder is disposed next to the user for the purpose of "filling" the unique contours of the sacro-lumbar region of the spine by providing a pressure for comfort to specific areas while controlling the overall stability of the thoracic spinal region. U.S. Pat. No. 4,552,135, issued Nov. 12, 1985 to Racz, et al., also shows a "Lumbar Belt" with a relatively large rear belt section superimposed over the small of the back, and an air-filled chamber disposed between the small of the back and the belt. U.S. Pat. No. 5,111,807 to Spahn et al. also discloses a back belt with a pressurizable air chamber in the lumbar region pad, along with unique connector means designed to couple the diverse materials of construction of the belt in a manner superior to that of conventional sewing. However, all of these devices, although designed primarily to constrain the range of motion of the wearer to prevent injury, also result in a compression of the lumbar area which can have little or no therapeutic value and, in some instances, can actually result in an increase in the likelihood of the wearer to sustain a compressive-type injury.

In conformance with the second category of back devices described above, braces and belts of various designs are used to support the lumbar region of the spine after it has been injured. An example of such a device is disclosed in U.S. Pat. No. 4,691,696 to de los Godos, which comprises a belt with one or more bracing structures designed to prevent torsional rotation of the wearer's back in the direction of an existing injury, thereby relieving stress from the injured area and providing an opportunity for the injury to heal.

Additional support braces exist in the prior art, such as that disclosed in U.S. Pat. No. 5,062,414 to Grim, which utilizes one or more fluid-filled chambers in the lumbar region of the belt, optionally in conjunction with electrically heated resistive elements designed to warm the injured area. Another example of a brace comprising fluid-filled bladders in a lumbar pad, along with electrically heated resistive elements, is disclosed in U.S. Pat. No. 4,702,235 to Hong. The Sports Plus II Belt, as shown in the AliMed catalog of 1995, on page S108, utilizes a plurality of vertically-oriented air-filled chambers that are distributed within the belt and extend beyond the lumbar region alone. However, these chambers are capable of expansion only in a radial direction and, thus, can serve only to tighten the belt circumferentially around the wearer's waist. Moreover, the Sports Plus II Belt has no horizontally disposed support members capable of transmitting vertically directed forces for relieving gravitational stresses on the lumbar region of the spine or creating a traction-like effect.

Additionally, there are several well known braces of the wrap-around corset type. Such corset braces wrap around the trunk of the body in the region of the lumbar spine. Such braces, however, are intended to reduce the compressive stress in the lumbar spine or to totally immobilize it. They are thus of limited value in the treatment of torsional or twisting injuries. In addition, they may be uncomfortable and difficult to fit to larger persons. Moreover, the highly constraining corset design imparts almost complete immobility to the torso of the wearer and is, therefore, ill-suited for use while pursuing day-to-day activities. Rigidly reinforced or rigid frame back braces are also well known. Such braces, however, also completely immobilize the entire spine. A patient using such a brace is rendered essentially disabled because he cannot move his spine in any way.

According to the third category of back devices described above, there are a number of braces and other such devices which are designed to provide active therapeutic benefit and to promote healing of the injured area. Generally, these devices can range from full-scale clinical appliances in the form of tables, chairs or other like structures, to belts and slings designed to be used in conjunction with large appliances. In theory, these devices function by suspending the weight of the affected patient in a manner that almost totally removes all gravitational stresses from the affected area of the spine. Thus, in contrast to the second category of devices described above, traction devices do far more than merely constrain the movement of the affected region of the body. Generally, they are part of an aggressive, non-surgical or post-surgical regimen designed to keep the spine free from torsional and compressive forces, thus allowing the injured area to heal as rapidly and effectively as possible. The major drawback of most tractional therapies is that, due to the complexity of the apparatus and the need for substantial intervention by an appropriately trained health care professional to assure proper therapeutic use and optimal benefit, they are suited only for use in controlled, clinical settings. The time that a patient spends in a normal traction device must be dedicated time during which the patient is incapable of participating in any other activities.

An example of an orthopedic lumbar traction brace used in conjunction with traction appliances is disclosed in U.S. Pat. No. 4,269,179 to Burton et al. The brace of the Burton et al. patent is designed to be attached to the lower rib cage of the patient. The patient, while wearing the device, is suspended through the supporting straps of the device from a multiple-position table which can be adjusted to an optimal angle to achieve a desired amount of gravity traction. Thus, the weight of the patient's upper body is suspended from the brace about the patient's lower rib area and the lumbar region of the spine is relieved of the normal gravitational stresses the patient's body weight would impose even when completely motionless in a standing or sitting position. In conformity with the general comments above, a patient using the brace and traction device disclosed in the Burton et al. patent would be precluded from engaging in physical activity of almost any kind.

U.S. Pat. No. 4,991,572 to Chases discloses another type of lumbar traction harness designed in theory to use the principles of gravity traction to relieve stresses from the lumbar spinal region, permitting efficient healing of the affected area. Unlike the device of the Burton et al. patent, the Chases device utilizes an air-inflated bladder to increase the comfort of a patient using the device for traction therapy. This device is basically a traction sling which is adaptable to use in a variety of conformations and patient alignments. This variety of configurations is best illustrated by reference to FIGS. 6–11 of the Chases reference. As disclosed in the reference, the principal advantage of this device is its flexibility of use, being adaptable to a number of patient orientations, unlike the majority of prior art traction table devices, whether mechanical or gravitational, such as those used in conjunction with the device of the Burton et al. patent. However, as is universally true of this type of therapeutic traction device, the patient undergoing therapy must dedicate the time to participate in the therapy and cannot pursue any normal day-to-day activities, whether or not employment-related, during therapy.

Similarly, treatment of cervical injuries or disorders often requires cervical traction for treating trauma to the muscles and ligaments of the neck and the cervical and upper thoracic vertebrae and associated spinal nerves. By applying cervical traction, a "cervical separation" is produced which alleviates pain caused by compression on the nerves, while allowing more blood flow to the affected tissue that speeds the healing process.

Normally, in the early stages of applying traction, cervical traction forces are most easily controlled when the patient is confined to a hospital bed where more complex and expensive traction equipment is carefully controlled by medical professionals. When the patient has reached a point in the healing process where such a level of clinical treatment is not needed, other controlled traction devices may be prescribed and used by the patient.

One such home use traction device is an "over-door" cervical traction system in which traction forces are applied to a head halter or harness placed under the chin and occipital lobe areas. (See *Flaghouse Rehab, Inc. Catalog,* 1933, p. 64.) The harness is connected to a hanger that attaches to a door and holds a water-filled weight bag that applies a controlled amount of upward traction force on the harness by gravity while the patient sits next to the door that supports the hanger and weight bag. This traction system applies traction forces by the weight bag pulling the harness upwardly from below the chin region and the base of the skull. The amount of water contained in a weight bag controls the amount of traction force. Although this system is useful, it requires a patient to sit in one place for long periods of time.

Another prior art patient-controlled cervical traction device is available under the name Pronex from Glacier Cross, Inc. This device includes a U-shaped block that fits behind the patient's neck and rests on the patient's shoulders. An air-inflatable bellows in the middle of the block applies lateral lifting forces upwardly to pillows on opposite sides of the patient's neck. This device requires the patient to be immobilized in a horizontal position while traction is applied. The traction force is not uniform around the entire neck region and the bellows, being located at the middle of the device, can apply undesired inward pressure to the middle of the patient's neck and windpipe. Such a device is similar in function and design to that disclosed in U.S. Pat. No. 5,441,479 to Chitwood, issued Aug. 15, 1995.

U.S. Pat. No. 5,403,266 to Bragg et al., issued Apr. 4, 1995, discloses a cervical traction collar that can be used by a patient to apply a controlled amount of traction-type force to the cervical region. The device of this patent uses a circumferentially-distributed air-inflated bladder disposed at the bottom edge of a rigid central brace portion similar to conventional rigid cervical braces (see, for example, U.S. Pat. No. 5,230,698 to Garth, issued Jul. 27, 1993). As the bladder inflates, the rigid brace portion is forced upward to towards the wearer's chin, exerting tractional forces on the cervical spinal region. However, significant disadvantages remain for a design of this sort in that the inflation of the circumferentially-distributed bladder is inevitably accompanied by a radial constriction of the wearer's lower neck region. The rigid neck brace portion of the device can also be a source of some discomfort to the wearer, thus diminishing the likelihood that the device will be worn for a sufficiently long period of time to optimize its clinical benefits.

Thus, each of the categories of spinal braces and devices described above, although useful, exhibit considerable drawbacks and inefficiencies. The first category of devices, those designed to prevent injury and/or to encourage proper lifting technique, are hampered by a limited efficacy. Furthermore, such devices generally act by compressing the lumbar region in a plurality of dimensions and, aside from restricting motion within a safe range, can possibly lead to an increased likelihood of certain types of back injuries. The second category of devices, those designed to protect an injured wearer while the wearer engages in physical activities, offers not much more protection than those devices designed to decrease the likelihood of initial injury. These latter devices function merely by restricting motion and/or by providing direct support to the lumbar or cervical regions. Certain devices are also capable of providing heat to the affected area as well. However, both of these initial categories of devices, although they permit the wearer some range of physical activity, can do no more to treat existing injuries than to minimize the likelihood of re-injuring an affected area, or aggravating an existing injury. They are incapable of providing active therapeutic benefits leading to enhanced healing of injuries of the various spinal regions. Despite whatever other utility these devices may display, the inability to actively promote healing is a significant drawback to these types of devices.

Back pain is common in normal pregnancy. More than 50% of all women experience some kind of back pain during pregnancy. Such pain can be classified into highback, lowback and posterior pelvic pain. Early studies have shown that for a successful treatment of back pain during pregnancy it is crucial to distinguish especially between low back pain (LBP) and posterior pelvic pain (PPP). At a glance these two conditions may share many characteristics in clinical status as well as in history, and therefore pregnant women with any type of back pain often have given the same kind of treatment or, more commonly, no treatment at all. Furthermore, some pregnant women suffer from both types of pain which complicates the situation. While LBP in pregnancy does not appear to differ substantially from the back pain well known in the general population, posterior pelvic pain is seldom found in men or among women who have never been pregnant and seems to be connected with the pregnancy hormones estrogen and relaxin.

To carry her pregnancy, the human female increases the lumbar curve, with a resultant disequilibrium of the vertical alignment of the body. There is a partial loss of abductor function of the gluteal muscles and wobbling. The hormone, relaxin, stretches all the lumbar and pelvic joints. This makes erect locomotion and even erect posture painful and tiring.

Erect posture is not only an unstable equilibrium, but a succession of unstable equilibrium's that manage to balance and correct each other. The result is a highly unstable equilibrium. In quadrupedal posture, it is the opposite; the center of gravity (CG) is low and the base of support is wide. In bipedal posture, it is the opposite; the CG is high and base support is narrow. This is main reason for instability of erect posture. How fragile and unstable erect posture is can be demonstrated in different ways. Humans takes the longest time to acquire perfect posture during infancy. It starts between 1 year and 18 months of age, but is not perfect until six to seven years of age.

Since erect posture is acquired and practiced before complete ossification, one can conclude that erect posture tremendously influences (in fact, determines) the anatomy of the human body and specifically the anatomy of the pelvis and spinal column during the time erect posture is being acquired.

In the study of orthopedic dysfunction of the human body one should never forget that for one billion years the body preceding humans was quadrupedal, the spinal column was horizontal, and the pelvis barely supported any structure. The whole orthostatics and orthodynamics of the mammalian body become altered when the truck rotated 90 degrees around the hip-joint area and the pelvis had to support the whole trunk.

Erect posture is not only a phylogenetic (genetic) inheritance, but also ontogenetic since the human infant starts out quadrupedal and only later switches to bipedalism. Quadrupedal ancestry is very well established in the human body and bipedal adaptation is very recent. The whole anatomy and physiology has had to readapt to a erect behavior, and this readaptation is not always perfect. The typical example to quote is the position of the heart within the chest. In quadrupedal posture, this organ peacefully rests on the sternum for a entire lifetime, while in and erect posture it floats in the middle of the chest with practically no strong anatomical support; all this predisposing the human heart to numerous heart conditions. The impression one gets from a review of the extinct forms that preceded Homo Sapiens is that present erect behavior is unstable and easily subjected to defects. There is hardly any organ of function in the human body that has not readapted to erect posture and locomotion.

Most current orthotic braces try to offer relief to back problems by the following; (1) Relieve Low Back Pain LBP, (2) Relieve Abdominal Muscle, (3) Reduce Leg Pain, (4) Stabilize the Pelvic Ring.

With respect to the product P.R.'s Mother-to-be, C.M.O. Inc., Barberton Ohio, the claim is made that the device prevents distortion of the lumbar curve, by transferring the weight of the abdomen. The abdomen exerts downward pressure on to the abdominal lift pad creating a greater pressure against the custom molded insert. This in turn is claimed to force the lordosis curve into its natural curve. Accordingly, it is reasoned that the greater the abdomen weight, the greater the support. The problem with the above device and those made similarly is that the device does not prevent distortion of the lumbar curve, but only transfer of the abdominal weight.

In 1854, Carpal Tunnel Syndrome was described as a complication of trauma. Today it is recognized as a extremely common entrapment syndrome.

The carpal tunnel area compresses or traps the median nerve inside the wrist. The median nerve is one of several nerves which allows a person to move the hand and fingers. Not much was known about Carpal Tunnel Syndrome by health care professionals until and extensive article on the subject was published by Dr. Phalen in the 1970. The carpal tunnel is surrounded by eight carpal bones and a ligament (flexor retinaculum). Flexor tendons and the median nerve pass through the tunnel. When the median nerve within the tunnel is compressed by edema (fluid retention) caused by swelling of tissue or damage, the resulting symptoms are termed as carpal tunnel syndrome (CTS).

As keyboard usage in the workplace has increased, CTS is becoming a much more common occurrence. In the case of worker compensation, CTS is becoming increasing claimed as being worked related. CTS most commonly affects women in mid-life, and often pregnant women have the symptoms (edema) that resolve postpartum. Patients often complain of frequent pain in the distal arm or wrists or into the thumb, index or middle fingers with a increased when the wrist is in motion. With the most common (95 percent) relating to the fact of awaking in the middle of the night with painful numbness in the hand. Up to 50 percent of patients have bilateral pain in both upper extremities, and often describe electrical sensations in the median area.

Nonsurgical therapy for carpal tunnel syndrome is indicated when (1) symptoms are less than one year, (2) muscle weakness or atrophy are not present, (3) deviations is not found on electromyographic needle examination and (4) only mild abnormality show up on nerve conduction studies. Nonsurgical therapy may include the following pharmaceuticals, bracing, and steroids injections.

Medications for CTS can be divided into two categories:

1. Nonsteroidal anti-inflammatories; reduce the swelling surrounding the effected joint compartment, such as Naprosyn(R), Feldrene(R), Ansaid(R), Daypro(R), Relafen (R), Lodine(R).

2. Analgesics; serve to reduce the amount of patient discomfort. Such as over the counter medications Tylenol (R), Percocet(R). Pharmaceuticals are short term methods of treatment since they typically do not address the source of the pain and inflammation in the tunnel compartment.

Palmar wrist splints worn at night may be suitable for patients whose symptoms are mainly at night. Although no ideal position for wrist splits is generally accepted, neutral mild extension is preferred to mild flexion. Wrist splints are usually used within the first three months of symptoms onset.

A further treatment of CTS is by steroid injection. Steroid injections in the wrists maybe have been shown to often be successful with injections such as triamcinolone acetonide and lidocaine. These may cause symptoms to temporarily worsen, but offer complete or significant pain relief in 60 to 70 percent of the patients for weeks to years. A significant relapse of symptoms may be seen on long term follow-up, however.

Surgical therapy for the treatment of CTS has two main operations; Carpal Tunnel Release and Endoscopic Surgery. Carpal tunnel release was first performed at the Mayo Clinic in 1941. It was one of the most common surgeries on the hand. An absolute indication for carpal tunnel release is muscular atrophy, discovered on examination of the thenar eminence following electrodiagnostic confirmation. Carpal tunnel release has a 15 to 20 percent failure rate. Endoscopic surgical techniques are now being used. The advantages of endoscopic surgery are smaller incision, shorter postoperative course, lack of palmar tenderness and less pain. Endoscopic surgery is a relatively new procedure, still on the steep side of the learning curve for many surgeons. Endoscopic surgery has the inability to fully visualized structures other than transverse carpal ligaments, with the inability to perform repair other than cutting ligament, and has the risk of lacerating digital nerves, arteries etc.

Surgery excepted, all the above mentioned treatments for CTS have a major drawback in that the reoccurrence and percent of patients treated effectively are a very small percentage of the patients affected. This is primarily due to the fact that the treatments do not reduce the main cause of CTS, which is irritating pressure in tunnel that causes nerve irritation. A device that acts to relieve this irritating pressure is needed.

SUMMARY OF THE INVENTION

Until now all maternal orthotic devices primarily worked in the same manner, in that the gravity weight and differential pressures were applied to the lumbar region by means of straps, braces and transfer to a lumbar pad. Thus gravity still exists and is only displaced. This cannot be readily shown to be a beneficial asset.

The design of the Pneumatic Dorsolumbar Maternal Support of the present invention provides the following benefits: the device provides a brace which selectively produces a "hyperextension" or "traction" or a "unloading" effect on the lumbar region, aiding both LBP and PPP . The lumbar extension sets located posteriorly on the back of the wearer create a vertical lift of the low back by lifting off of the pelvic region. The lumbar curve or lordosis curve can be controlled by the use of bladders that curve upon inflation. This assists or reduces the amount of lumbar curve. The pelvic pillow provides both a vertical lift and a pelvic support. The lower pelvic belt provides stabilization in the pelvic ring and transfers weight of the abdomen posteriorly to the sacrum. The addition of front anterior extender sets assist in the "unloading" process by assisting the lumbar extender sets in the weight bearing load. The extender sets also serve as a counterbalance to effect "Disc-Equilibrium" by changing the direction of the applied forces in the lumbar region. To increase lumbar curve, a pneumatic lumbar support pillow may also be attached. With this system, the wearer is able to control ambulatory traction while still performing everyday activities.

The inflatable carpal tunnel glove of the present invention creates a new approach toward the treatment of CTS. A difference in the effects of the present invention as compares to existing devices is that the present invention is a pneumatically controlled ambulatory hyperextension orthotic glove providing for mild traction of the tunnel compartment. The traction is wearer controlled. Further, cooling effects are provided for to relieve swelling (edema) and produce a reduction of the pressure on the median nerve. With a dual control pump, the wearer can control flexion or extension of the wrist.

The present invention is an ambulatory, wearable support to be worn by a person for applying an extending force to a portion of the human anatomy while being worn, the portion of the human anatomy having an anterior portion and an opposed posterior portion, includes a first anchor member substantially encircling a first portion of the human anatomy, A second anchor member is spaced apart from the first anchor member, the portion of the human anatomy that is to be subjected to the extending force being disposed substantially between said first and second anchor members. A plurality of extender sets have at least one selectively inflatable bladder. The at least one bladder has a first end operably coupled to the first anchor member and a second end operably coupled to the second anchor member, the plurality of extender sets being spaced apart and disposed both anteriorly and posteriorly with respect to the portion of the human anatomy that is to be subjected to the extending force. In preferred embodiments, the ambulatory, wearable support comprise a maternal support and a wrist support

BRIEF DESCRIPTION OF THE DRAWINGS

FIG. 3, provided in two panels, illustrates the relationship of the anatomy of the ribs to the spine: panel A is a lateral view of ribs and spine; panel B is a partial sectional view of the skeletal anatomy of the ribs and spine, taken along line 3—3 of FIG. 3a;

FIG. 4 illustrates a partial cut-out perspective view of the vertical support members of the invention;

FIG. 5 is an illustration of an air-inflatable bladder of the present invention incorporating a vertically expanding bellows portion;

FIG. 6 provides an illustration of the vertical support members of the device of the invention further illustrating the receiving cup members affixed to the upper and lower horizontal support members of the vest;

FIG. 7 provides, in perspective, an illustration of inflation means for the vest of the invention;

FIG. 8 provides an illustration of an alternative embodiment of the inflation means of the present invention; and FIG. 9 provides an illustration of an alternative embodiment of the present invention, a cervical traction brace.

FIG. 10 is an elevational view of the maternal support vest of the present invention depicted in the open configuration view the inside of the vest with the extender sets depicted in phantom;

FIG. 10a is a perspective view of a pair of shorts that are optionally used in conjunction with the vest of FIG. 10;

FIG. 10b is a side elevational view of a pair of shorts that are optionally used in conjunction with the vest of FIG. 10;

FIG. 10c is a rear elevational view of a pair of shorts that are optionally used in conjunction with the vest of FIG. 10;

FIG. 11 is an elevational view of the maternal support vest of the present invention depicted as in FIG. 10 with the shorts of FIG. 10a affixed to the vest and depicted in a front elevational view;

FIG. 12 is a perspective view of the vest of FIG. 10 and the shorts of FIG. 10a as worn by a pregnant female person;

FIG. 12a is a rear elevational view of the vest of FIG. 10 and the shorts of FIG. 10a as worn by a pregnant female person;

FIG. 13 is a perspective view of a second embodiment of the present invention, the upper support being integrated with a body suit as worn by a pregnant female person;

FIG. 13a is a side view of the embodiment of FIG. 13;

FIG. 13b is a rear view of the embodiment of FIG. 13;

FIG. 14 is a perspective view of the inflatable devices of the present invention independently, fluidly coupled to an inflation/deflation valve;

FIG. 17a is an anterior perspective view of the liner of the wrist support of the present invention in relation to the hand of a wearer;

FIG. 17b is an posterior perspective view of the liner of FIG. 17a;

FIG. 18a is an anterior perspective view of the of the outer sheath superimposed on the liner of the wrist support;

FIG. 18b is an posterior perspective view of the liner of FIG. 17b secured to the lower arm of the wearer;

FIG. 19a is an anterior perspective view of the of the outer sheath superimposed on the liner of the wrist support and secured to the lower arm of the wearer;

FIG. 19b is an posterior perspective view of the outer sheath of FIG. 19a;

DETAILED DESCRIPTION OF THE PREFERRED EMBODIMENTS

Figure 1:
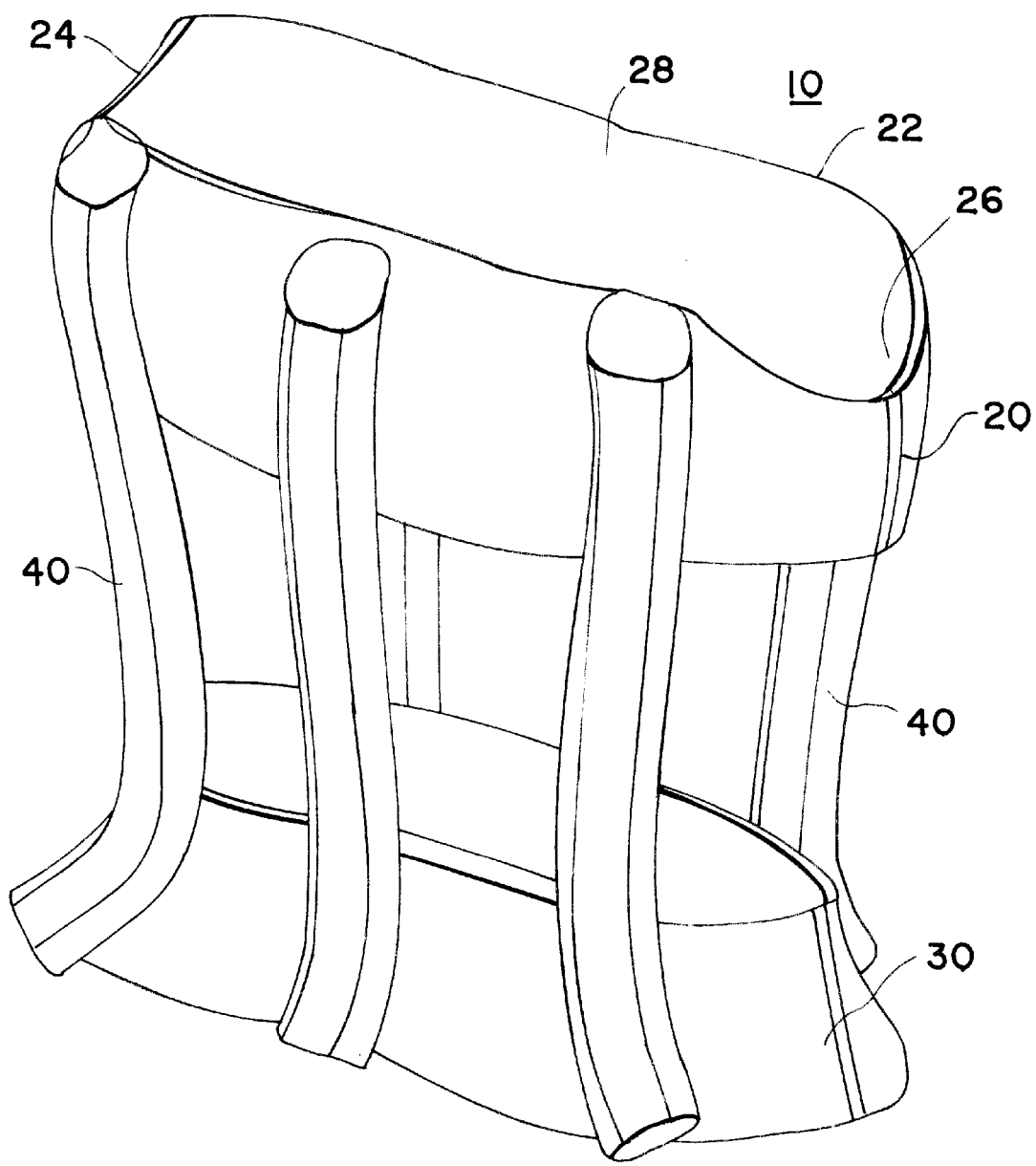
FIG. 1 provides a generalized perspective illustration of an embodiment of the inflatable traction device of the invention.

Referring now to FIG. 1, there is depicted at 10 a generalized perspective illustration of a first embodiment of the inflatable traction device of the invention, presented with a level of detail sufficient to inform the skilled practitioner of the concept and the practice of the invention. The embodiment illustrated in FIG. 1 is adapted for use as a lumbar traction vest. As can be seen in FIG. 1, the traction vest of the invention 10 is comprised of an upper horizontal support member 20, a lower horizontal support, or belt, member 30, and a plurality of individual, vertically-inflatable support members 40.

As depicted in FIG. 1, the embodiment of the present invention provides a generalized level of detail. The upper horizontal support member 20 is depicted as a unit of one-piece construction. In practice, there are a variety of constructions that are functional for the upper horizontal support member 20. To one of ordinary skill in the appropriate area of art, it will be apparent that the choice of which of these various methods of construction are utilized to prepare an embodiment of the present invention will be determined by such factors as available materials, cost, durability, comfort, and the like. Perhaps the simplest method of construction for the upper torso member 20 would be to utilize an elasticized material such as would be used in the fabrication of support undergarments.

As is depicted in FIG. 1, the upper horizontal support member has a top edge 22. The contour followed by the top edge 22 is designed to allow the arms of the wearer to extend comfortably above the upper member 20. Toward this end, the upper horizontal support member has a right arm access contour 24, and a left arm access contour 26. If a one-piece unitary construction is utilized for the upper horizontal support member 20, then it is anticipated that the lumbar traction vest of the present embodiment of the invention would be donned by the wearer by first slipping the arms and head through the upper support member 20.

A key consideration to weigh in the selection of design materials and in the actual construction of the upper member would be the ultimate comfort of the wearer. This comfort would depend to a large extent on the degree of flexibility of the material of construction of the upper horizontal support member 20, as well as the size of the wearer and the actual fabric of construction. It will be recognized that certain materials of construction, such as certain kinds of plastic and the like, would have lower degrees of flexibility and also could prove to be uncomfortable to the wearer in that they would make it difficult for circulation of air between the inside surface 28 of the upper member, and the outer surface of the wearer. Of additional consideration in this regard would be the ability of the material of construction to "breath" sufficiently to allow the passage of moisture from the skin of the wearer to the atmosphere. With this in mind, materials such as plastics would be less suitable than the type of flexible fabric material normally associated with elasticized support undergarments.

Alternatively, as would be recognized by one of skill in the art, a variety of other designs could be used for the construction of the upper member. The upper support member 20 could be constructed of a semi-flexible material, or even a canvas or nylon of sufficient strength, with an opening disposed either to the front, to the rear, or to either side of the torso, wherein the opening may be secured by adjustable means such as laces, buckles, or Velcro™-type hook and loop closures. With a construction requiring closure in such fashion, the wearer could don the vest in a simpler manner, one that is similar to donning a regular garment. Construction of the upper support member 20 requiring closure in this manner would also provide additional means to adjust the fit of the vest to the wearer, if necessary. As will be apparent from the description below, the fit of the upper member can be critical in that it is an essential element in the transfer of gravitational forces to the proper structural elements of the vest of the present embodiment.

The lower horizontal support, or belt, member 30 is depicted in FIG. 1 in a single unitary construction. Although it is theoretically possible, utilizing materials of sufficient flexibility and stretch, to so construct the lower horizontal member, preferably it is advisable to construct the lower member along the lines of a conventional front-buckling belt for the embodiment depicted in FIG. 1. Once again, both the specifics of construction, as well as the material choices, for the lower horizontal member 30 depend upon a number of practical factors, such as availability, comfort, cost, and the like. It is contemplated that the lower support or belt member 30 can most practically be constructed from readily available weight-supporting belts such as those utilized in conjunction with external frame backpacks.

As used with those devices, these types of belts are designed to distribute the bulk of the gravitational forces exerted through the entire apparatus to a portion of the wearer's body, namely the hips, that is best suited to bear that load. These types of belts are typically worn fairly low on the hips and are tightened snugly thereto to ensure that the distribution of forces is accomplished in an efficient and effective manner. In a like fashion, the lower horizontal support member 30 of the lumbar traction vest 10 is designed to receive the bulk of the weight-related forces acting on the vest 10, and transfer those forces to the wearer's hips. It should be recognized here that the phenomenon that occurs through this weight transfer mechanism is essentially the same phenomenon that produces the therapeutic effect of large traction appliances used in clinical settings. In the practice of the present invention, the weight of the upper body of the wearer is essentially hung from the upper torso member 20, and distributed through the inflatable support members 40 to the lower belt member 30. Thus, the weight forces normally experienced by the spinal region affected by this or any other embodiment of the present invention are instead carried by anatomical structures, such as the hips of the wearer for the lumbar vest, best suited for carrying such a load, leaving the vertebrae of the affected spinal region free from compressional and torsional stress and, therefore, allowing injured spinal anatomy a chance to heal properly. Once again, this is the same basic concept that is in operation in the use of full-sized mechanical traction appliances such as those of the prior art discussed above.

Figure 2:
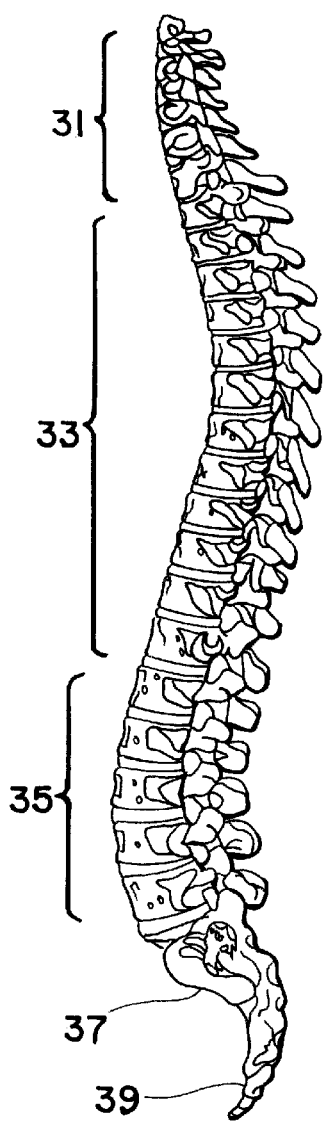
FIG. 2 provides a lateral view of the human spine, illustrating the various spinal regions: the cervical, the thoracic, the lumbar, the sacral and the coccyx.
Figure 3A:
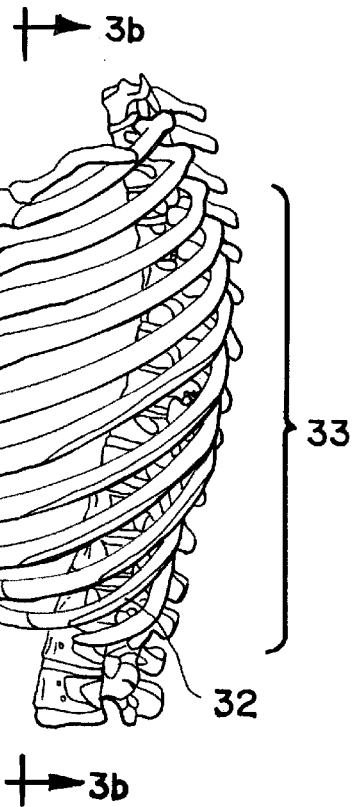
Figure 3B:
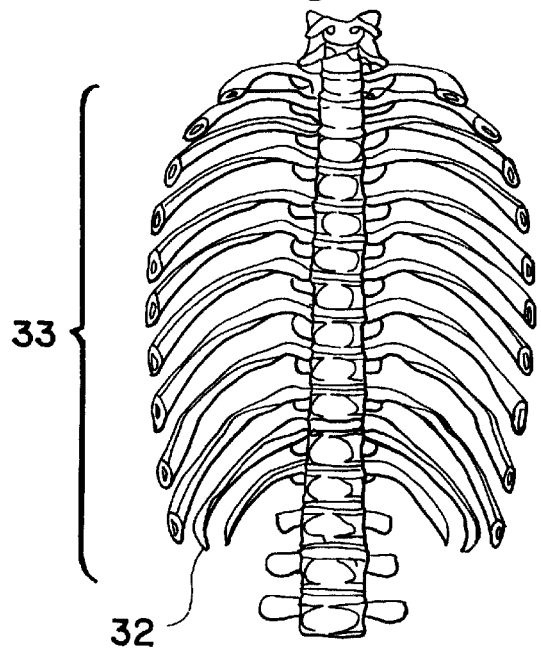

As has been demonstrated through the use of large-scale gravitational traction devices, the mechanical transfer of gravitational forces necessary to produce the desired traction effect, where these forces are removed or significantly reduced from the lumbar region of the spine, is achieved through the leveraging of skeletal structures associated with the upper spinal region. By reference to FIG. 2, and in accord with the discussion above, there is illustrated a lateral view of the human spine comprising thirty-three bones—seven of the cervical region 31, twelve of the thoracic region 33, and the five of the lumbar vertebrae 35, with the latter merging endwardly into the five fused sacral 37, and the four fused coccyx vertebrae 39. The relationship between the various spinal regions and the ribs is illustrated in FIG. 3 where, in panel A, there is illustrated a lateral view of the ribs, along with the associated spinal regions, primarily the thoracic 33. In FIG. 3b, there is illustrated a partial sectional view of the skeletal anatomy of the ribs and spine, taken along line 3—3 of FIG. 3a. As these figures illustrate, the ribs, including the lowest "false" ribs, are integral with the twelve thoracic vertebrae.

In the practice of the present invention, the upper horizontal support member 20 effectively grasps the ribs primarily, although not exclusively, along the lower region. This "grabbing" of the ribs in the initial step in the mechanical transfer of forces away from the lumbar region of the spine. In this fashion, the ribs, "grabbed" by the upper horizontal support member, act as a lever to transfer the applied forces to and from the upper spinal region, most probably the T1 to T5 vertebrae and associated rib structure. The vertically oriented inflatable support members 40 form the next link in the mechanical chain through which forces are removed from the lumbar region of the spine. Ultimately, through the inflatable support members 40, the forces that are normally borne by the lumbar vertebrae 35 and associated disc anatomy are transferred to the lower horizontal member 30 and onto the wearer's hips.

In light of the "mechanics" by which the device of this embodiment of the present invention functions, it should be apparent to one of skill in the art that the structure of the upper horizontal support member 20 must meet the relatively simple criterion of being able to effectively and firmly grasp the rib cage so as to use the ribs to lever the applied forces to and from the upper thoracic vertebrae. In light of this criterion, a wide range of structural arrangements for the upper support member 20 are possible. The principal benefit of this design flexibility is that the device of the invention is capable of being fabricated in a lightweight and comfortable form, appropriate for ambulatory use over extended periods of time. As important, the construction of the lumbar traction vest 10 of the above-described embodiment is such that the vest possesses sufficient flexibility to allow the wearer to engage in a reasonable range of physical activity, all without imparting undue stress to the injured spinal region. This same principle is in operation, although to a less noticeable extent, for embodiments of the invention designed to affect the cervical region of the spine.

As discussed immediately above, key elements in accomplishing the transfer of forces in the traction vest embodiment to the lower support member, while at the same time maintaining flexibility of the vest that permits the wearer to engage in moderate levels of physical activity, are the vertical inflatable support members 40. As illustrated in FIG. 1, the inflatable lumbar traction vest 10 of the instant embodiment is shown with five vertical inflatable support members 40. Although the exact number of support members 40 incorporated into the design of the traction vest 10 is important, it is not critical to achieving the desired function of the vest that there specifically be five vertical members. The inventor considers five vertical members to be an ideal, although not essential, configuration. Such a number of support members 40 provides sufficient support between the upper and lower members of the vest, as well as allowing for sufficient flexibility to permit the wearer a reasonable range of activities while wearing the vest.

In determining an optimal number of support members for a particular embodiment of the present invention, the most critical factor is the total amount of force which the device must be able to apply to the affected region of the spine. In the embodiment described above for a traction vest designed to affect the lumber region of the spine, the most practical starting point for determining the force that needs to be applied, and from that the optimal number of vertical support members, is a direct comparison to the type of traction appliances referred to above with respect to the discussion of U.S. Pat. No. 4,269,179 to Burton et al. In a Burton-type traction device, the maximum amount of force that could be applied to a patient's lumbar spinal region would be equal to approximately 40–50% of that patient's body weight. This would represent an upper boundary for such a range of forces, in that to achieve that amount of force through a traction device, the inclined table on which the patient would be suspended would have to be at a maximum angle of inclination approaching the vertical. In such an extreme position, the patient's weight from the lower half of the body would be suspended from the traction device. Thus, for a 200-lb. man, the maximum expected force to be applied to the lumbar region through the gravitational traction device would be approximately 80–100 pounds.

In any embodiment of the present invention, the maximum amount of force exerted on the affected spinal region through a vertical support member of the device would be a function of the gas pressure within the inflatable member and the horizontal cross-section of the support member. If we assume for sake of simplicity that the vertical support member is in a cylindrical configuration and that the horizontal cross-section of the member is simply the area of the end of the cylinder, then the force exerted by that support member can be described by the following equation:

$$F = P\pi r^2, \qquad (1)$$

where F is the force, P is the inflation pressure of the support member r is the radius of the cylindrical support member and π is the familiar mathematical constant. Where there is a plurality of vertical support members for an embodiment of the present invention, then the total force, $F_{tot}$, exerted on the affected spinal region through the traction device will be simply the sum of the forces exerted through each of the support members. For n vertical support members, each of the radius $r_n$, then Equation (1) can be expressed as follows:

$$F_{tot} = (P_1 P \pi r^2_1) + (P_2 P \pi r^2_2) + \ldots (P_n P \pi r^2_n) \qquad (2)$$

For the expected situation where all of the vertical support members are of the same radius (r) and inflated to the same gas pressure (P), then Equation (2) can be simplified to the following expressions:

$$F_{tot} = nP\pi r^2, \qquad (3)$$

where n is the number of inflatable vertical support members. Thus, using Equation (3), it is possible to determine the optimal number of support members to achieve a desired total force at a specific target inflation pressure and radius. Of course, other calculations are possible using Equation (3), depending on the particular variable being optimized and the other information available.

Thus, it will be recognized by one of appropriate skill that the actual number of vertical support members 40 can be fewer than five, or more than five. Generally speaking, it would be undesirable for the number of inflatable support members to be less than four. With a configuration of four vertical support members, these would preferably be distributed with two in the front of the vest and two in the rear of the vest. It is also possible to have more than five members, such as six, where the plurality of vertical inflatable support members 40 would be distributed equally between the front and back portions of the vest 10. It is also contemplated that a greater number of vertical support members 40 may be desirable for some applications where greater levels of constraint of movement may be preferable, such as those designed to correct deviations in spinal conformation typical of conditions such as scoliosis, lordosis or kyphosis.

There also exists a practical limit on the upper number of vertical support members 40 used in the vest. A significant, advantageous feature of the vertical orientation of the inflatable support members of the invention lies in the fact that such an orientation leads directly to the mechanical distribution of forces vertically within the vest 10. This is achieved through a vertical distribution forces through the inflatable support members that effectively results in the suspension of a major proportion of the wearer's body weight from the upper horizontal support member which weight, in turn, is transferred to and supported by the lower horizontal support member or belt, in the case of the traction vest embodiment. Alternative orientations of inflatable members, for example in a horizontal orientation or in a torroidal configuration, could lead directly to spinal compression, as opposed to spinal support or re-distribution of forces acting on the spine. Thus, inflation of a horizontally-oriented bladder system could result in the same type of effect evidenced with prior art corset-type braces discussed above which can significantly immobilize the wearer. It is contemplated that a similar effect could result from the use of too many vertical inflatable members in the design of the vest of the present invention.

As shown in FIG. 1, the plurality of vertical support members 40 are of approximately equal diameter, which diameter is approximately 1 inch or more, although individual members may have a slightly different conformation depending upon their relative positions on the vest 10. Essential to the effective function of these vertical support members are the air-inflatable bladders 50, as illustrated in FIG. 4 in partial cut-away section. The embodiment of the present invention illustrated in FIG. 4 contemplates but a single inflatable bladder 50 present in each of the vertical support members 40. However, it will be recognized that it is possible for a plurality of essentially cylindrical bladders to be utilized in each vertical support member 40, each of the plurality in fluid communication so that a single source of air or other suitable gas would be capable of inflating the plurality of bladders 50 in a single vertical support member 40. It is also contemplated, as illustrated in FIG. 5, that the bladders can be constructed of a bellows design to further aid in the upward vertical expansion, and subsequent vertical distribution of forces, of the support members 40. As shown, in FIG. 5, the individual bladders may be advantageously constructed with at least one bellows portion 55, although it is possible to construct any one bladder 50 with a plurality of such bellows portions.

The bladders 50 may be constructed of a variety of materials possessing the desirable characteristics of flexibility and strength. However, it is contemplated that the preferable material of construction of the bladders 50 be latex due to the ease of fabrication possible with such material. Such material can be fabricated into appropriate bladders by specialty manufacturers such as North American Latex of Sullivan, Ind. As contemplated by this embodiment of the present invention, the diameter of the bladders 50 controls the diameter of the inflatable support members 40. Given the use of latex as the material of the bladders, a maximum practical diameter of the cylindrically-shaped bladders would be about 1 inch. Latex bladders of this diameter would be safely capable of inflation to a maximum pressure of approximately 20 lbs/in$^2$. However, it is necessary to inflate the bladders 50 only to a pressure in the range of 6–12 lbs/in$^2$ (see Equation (3)) to achieve the desired mechanical characteristics of the vertical support members, at least for the majority of contemplated applications of the lumbar traction vest embodiment. Variation in the range of inflation pressure can also be achieved through selection of the material of construction of the bladders, as well as the number of vertical support members 40 utilized on the vest, and the number of bladder segments within any one support member 40. In the context of inflation pressure, it is important to remember that it is desired to retain a sufficient degree of flexibility in the fully inflated vest so that the wearer will not be so constrained in movement as to be practically immobile. For the majority of applications contemplated for the vest 10, it will remain preferable for the wearer to be free to engage in a reasonable degree of physical movement while wearing the vest. This is where selection of the material of construction of the bladders 50 becomes important; latex is particularly advantageous in that it is capable of maintaining sufficient flexibility when inflated to the desired level of pressure.

An additional consideration in the inflation of the vertical support members 40 is that it is preferable to have a mechanical means for constraining the radial expansion of the bladders during inflation. As explained at some length above, the traction effect of the device of the invention is achieved through vertical distribution of forces through the support members. To the extent that the inflatable bladders also expand radially (horizontally), no benefit is derived for the practice of the invention. The means for constraining radial inflation could be the outer portion 43 of the vertical support members 40. It could also be provided by a sheath surrounding the bladders 50, where the sheath is fabricated of a sufficiently stiff material. It is also possible that the walls of the bladders themselves could be integrally constructed with a material capable of vertical but not horizontal expansion upon inflation.

Depending upon the choice of material of construction for both the bladder and the outer portion 43 of the vertical support members, it may be necessary to incorporate additional support means into the bladders and/or the vertical support members. These additional support means serve the purpose of imparting additional stiffness, and therefore support, to the vertical support means. Suitable material of construction for these additional support means may be wood, plastic or even metal. In the case of plastic, the individual additional support means may then be advantageously fabricated to a contour that matches the wearer's body contours. It is also possible to fabricate individual bladders 50 incorporating support means in the form of a flexible fabric material integrally constructed with the walls of the bladder.

Alternatively, for an application where it is desirable for the inflatable vest of the present invention to impose mechanical restraints on anatomical structures of the wearer's spinal region, as would be the case where the vest was utilized to import a construction to a mis-aligned spine typical of conditions such as scoliosis, lordosis or kyphosis, the additional support means may be constructed of a less flexible, stiffer material, preferably pre-molded to a desired conformation.

An additional consideration in the function of the vertical support members is the material of construction of the outer portion 43 of the members 40. The specific material of construction chosen here is less critical than the choice of bladder material and will typically be driven by cost, availability and, to a lesser extent, comfort. It is possible for the outer portion of the vertical members to be constructed from such materials as canvas or nylon, although nylon would be preferable due to weight considerations. An additional function of the outer portion 43 of the vertical members 40, as mentioned above, is to constrain the inflation of the bladders 50 and to physically limit the expansion of the flexible bladders in a radial direction upon inflation, making possible the vertical distribution of forces.

The vertical support members 40 can be mechanically affixed to the upper support member 20 and the lower member by a variety of means. As illustrated in FIG. 6, each end of the vertical support members is placed in receiving cup members 45 permanently affixed to the vertical members of the vest by a variety of means, such as gluing, sewing, and the like. It is also contemplated that the vertical support members can be directly coupled to the horizontal members of the vest 20 without the use of receiving cup members. It is also contemplated that the overall design of the vest embodiments be more unitary than is apparent from the depiction in FIG. 1. Thus, it may be advantageous to incorporate means for affixing vertical support means to the upper and lower horizontal support members integrally into a one-piece design which would provide an appearance that more closely resembles a typical vest worn as clothing. This would provide additional advantages in that the overall aesthetic appeal of the device would be enhanced. Since it is envisioned that the device of the present invention would be capable of being worn for extended periods of time, such considerations may be of some significance in a practical context. However, there are a variety of engineering and manufacturing considerations that will dictate the overall design of the vest, as well as the specific means of coupling the vertical support members 40 to the upper torso member 20 and the lower belt member 30. Such choices should be well within the experience of a practitioner of appropriate level of skill in the art. It should be noted that a primary consideration in the overall design of the upper and lower horizontal support members and how they interact mechanically with the vertical support members is that there must be a mechanical coupling between these structural elements so that the vertical forces generated by the expansion of the bladders 50 are in turn transmitted to the upper and lower horizontal members to achieve the desired traction effect.

Inflation of the bladders 50 disposed inside the vertical support members may be accomplished by a variety of means, as would be apparent to a skilled practitioner. One of these is illustrated in FIG. 7. Illustrated therein is a hand pump mechanism shown generally at 60. This pump mechanism 60 comprises a removable pumping bulb 62, a pressure fitting 64, and a bladder access port 66. The bladder access port is, in turn, in fluid communication with a bladder channel 68 through which air is forced by hand squeezing of the pumping bulb 62. Such pressure fitting could be a common Schraeder-type valve typically found on bicycle and car tires. With such a fitting, pressure inside the bladders could be relieved through the simple act of depressing the central valve stem in the fitting. Alternatively, a Velcro™-type hook and loop closure (not shown) could be provided to cover the non-removable components of the inflation mechanism 60 when not in use.

It is contemplated that each of a plurality of inflation mechanisms 60 be in fluid communication with each of a plurality of bladders distributed throughout the vertical support members. In this fashion, it would be possible to selectively tailor the inflation pressure within the device to provide lesser pressure in some regions of the device, and greater pressure in others. It is contemplated that this type of custom adjustment of the inflatable bladder system of the device of the invention could be achieved to result in whatever degree of motion would be desired for a particular activity contemplated for the wearer. The number and distribution of such separate bladders within the bladder system of the vest would be limited by such practical considerations as the complexity of manufacture, the resulting costs of multiple-component systems, and the specific applications of the device. In addition, it is contemplated that an additional bladder, preferably in fluid communication with one or more of the vertically-oriented bladders, be placed so as to conform to the unique geometry of the lumbar curvature of the wearer's back.

It is also contemplated that alternative mechanisms be utilized for pressurizing the bladder system of the device. One of these is illustrated in FIG. 8. The mechanism contemplated here is a completely enclosed pump means 65 which is activated by downward pressure of the wearer's thumb on the convex surface of the pump means. Such systems find frequent use in inflatable sporting apparati. Usually associated with such inflation means are hand-operated pressure release valves (not shown) so that the air pressure within the bladders 50 may be relieved to facilitate the removal of the vest 10 from the wearer.

An alternative means for inflation of the bladder system within the vest is possible in conjunction with an important anticipated application of the lumbar traction vest embodiment of the invention. Currently, long-haul truck drivers are frequently beset with a variety of lower back ailments stemming from the repetitive bouncing and jarring such drivers experience during long hours of driving. Such conditions are often aggravated by the fact that these drivers frequently must go directly from long hours of driving, with accompanying stresses applied to the lower spinal regions, to unloading of the transported goods from their trucks at a given destination. If such lifting is not preceded by appropriate stretching of the lower back regions and warming up of the muscles involved in heavy lifting, then the chances of injury to the lower back become much higher. If the driver does not follow proper lifting technique, then the situation is exacerbated. The vest of this embodiment of the present invention provides an ideal means for such long-haul drivers to avoid injury to their lower backs, as well as aggravation of existing injuries during long hours behind the wheel. A significant advantage of the lumbar vest embodiment of the present invention, as described above, is that it is capable of being worn during a wide range of physical activity. Furthermore, it is comfortable enough to be worn for relatively long periods of time so that, even if the degree of therapeutic effect does not rise to the level associated with clinical traction appliances, the overall effect of the use of the vest embodiment of the invention can match or exceed that of the large appliances. Such characteristics make the vest of the present invention ideally suited for use by long haul truckers.

Most large tractor/trailer combinations employ a compressed air apparatus associated with the brake system of the truck. It is relatively easy to utilize a means to tap into that source of pressurized air and extend a hose and coupling means into the cabin of the truck for inflation of the bladders of the vest while the wearer is driving the truck. Connection to the compressed air system of the truck can be achieved by mechanical hose coupling devices such as a luer lock fitting. Thus, the wearer can inflate the vest while driving to a level of pressure that is personally comfortable, arrive at the scheduled destination, further adjust the inflation level using the air hose means, and then immediately upon parking the trucks, begin to unload cargo while still wearing the vest of the invention, and after uncoupling from the air hose means. The embodiments of the present invention disclosed herein are uniquely capable due to their light weight and flexibility to meet various federal and state drivers' safety requirements for devices worn while operating commercial vehicles in the transport of goods in commerce.

Regardless of what mechanical means is used to bring pressurizing gases to the bladder system of the vest, the present invention contemplates the use of a check valve associated with each separate gas flow/bladder system within the vest so that there is no chance of an over-inflation occurring during wearing of the vest. Valves of this nature are well known in the art. Typically, such valves can be selected or set to match the maximum rated inflation pressures of the individual bladders. Thus, when the pressure rises to the safe limit of a bladder, either during inflation or during use, the check valve will activate to relieve the buildup of pressure before damage can occur to the vest, or injury to the wearer.

FIG. 9 illustrates an alternative embodiment of the present invention, shown generally at 70, designed to affect the cervical region of the spine. As depicted in FIG. 9, the cervical brace 70 is shown in a generalized, almost schematic, fashion designed to illustrate the main elements of the brace on a level of gross detail. FIG. 9 illustrates that the cervical brace 70 is comprised of at least three major components, an upper mandible support member 74, a lower clavicle support member 76, and a central bladder-containing portion 78. Disposed within the central bladder-containing portion 78 are a plurality of individual, vertically-inflating bladders 50, shown in FIG. 9, in partial cutaway view, with an optional bellows portion 55. The number and diameter of such bladders 55 can be calculated in accord with Equation (3) above, as was described previously with the lumbar vest embodiment of the present invention. The exact construction of the central bladder-containing portion 78 of the present embodiment is subject, as with the previous embodiment, to substantial variability, as will be recognized by one of skill in the appropriate art. It is contemplated that the central portion 78 be constructed or a flexible fabric material onto which are affixed separate chambers within which are contained each of the plurality of bladders 50. It is also contemplated, by way of example only and without limitation, that the central portion 78 may be constructed of a foam material from which are excised suitable volumes for containing the vertically-expanding bladders 50.

As illustrated in FIG. 9, the central bladder-containing portion 78 of the cervical brace 70 also comprises a support region 86 disposed to be oriented to the back of the wearer's neck and designed to provide sufficient support in a front-to-back plane so as to restrict the range of motion to the rear of the wearer's head. Also shown in FIG. 9 is a means 88 for adjustably fastening the cervical brace 70 around a wearer's neck. FIG. 9, in addition, illustrates a pumping mechanism 60 through which the bladder system within the cervical brace 70 is inflated to a target pressure. Based upon analogy to existing mechanical traction devices, an optimal force to be achieved for cervical traction through use of this embodiment of the present invention would be approximately 15–25 pounds. Such an inflation mechanism comprises similarly-numbered elements as that for the mechanism of the embodiment of FIG. 7.

FIG. 9 illustrates the upper and lower support members of the cervical brace 70 at a gross level of detail only. It is contemplated that each of the horizontally disposed support members of the brace comprise additional detail, as would be appreciated by a skilled practitioner. For example, the upper or mandible support member may be contoured to fit the anatomical details of the wearer's chin and jaw area in order to attain a more effective fit of the brace to the individual wearer. It is contemplated that the upper support member 74 will be fabricated preferably of a relatively dense plastic foam in order to both provide support and resistance to the vertically directed forces acting through the brace, at the same time providing comfort to the wearer. Optionally, it is contemplated that the upper support member 74 may be covered with a comfortable, breathable fabric because it will be in direct contact with the wearer's skin for a segment of the support member's length.

The lower or clavicle support member 76 is also illustrated in FIG. 9 at a level of gross detail only. It is contemplated that this portion of the cervical traction brace 70 may assume a plurality of embodiments. In one embodiment, it may be constructed in a similar manner and of a similar material as the upper support member 74. Alternatively, it may also comprise an air-inflatable bladder, either with separate inflation means, or in direct fluid contact with the bladder system of the central bladder-containing portion 78. Regardless of the actual manner of construction selected for either of the two horizontally directed support members of the cervical brace 70, they must be designed so as to be able to withstand, and transmit where appropriate, the traction forces acting vertically through the brace. Although constructed on a smaller scale than the lumbar traction vest embodiment described above, the inflatable cervical traction brace of FIG. 9 functions on identical principles to those described for the previous embodiment. As the bladders are inflated, they expand vertically, exerting traction forces on the cervical region of the wearer's spine. The weight of the wearer's head is supported by the upper or mandible support member 74 and transmitted through the central bladder-containing portion 78 to the lower or clavicle support member. Thus, the gravitational forces acting on the wearer's cervical spinal region are relieved and actually borne by the wearer's upper chest and shoulder area, depending on the specific design of the lower support member. The end result is essentially identical to that obtained with the type of mechanical cervical traction devices described in the Background of the Invention section, supra. The advantage, therefore, of the present invention is that the therapeutic gains to be realized from traction treatment can be achieved without resort to immobilizing the patient, with a resultant loss of productive time.

A further embodiment of the present invention is depicted in FIGS. 10, 10a–10c and 11. This embodiment is a maternal support indicated generally at 100. The maternal support 100 is comprised generally of a vest 102 and shorts 104. The vest 102 is depicted in FIG. 10 and the separate shorts are depicted in FIG. 10a. In FIG. 11, the vest 102 and the shorts 104 are integrated into a unitary maternal support 100.

The vest 102 in FIGS. 10 and 11 has three major components: upper anchor 120, lower anchor 122, and extender sets 124. The upper anchor 120 has a torso section 134. The torso section 134 is formed of a flexible material that is only minimally stretchable in either the vertical or horizontal direction, as depicted in FIGS. 10 and 11. Preferably, torso section 134 exhibits enhanced grip ability with respect to the skin surface of a wearing person. The enhanced grip ability of torso section 134 provides for minimal slippage between the torso of the wearing person and the torso section 134. A pair of shoulder straps 136 are affixed at both ends thereof to the torso section 134. It is understood that adjustability of the length of the shoulder straps 136 may be provided by the inclusion of buckles or loop and hook type fasteners, as desired.

The torso section 134 is designed to substantially encircle the torso of a wearing person in order to accommodate different sized wearers. A plurality of adjustable torso straps are provided. In the embodiment depicted in FIGS. 10 and 11, three generally parallel torso straps 138 are provided. It is understood that fewer than three torso straps 138 or more than three torso straps 138 may be utilized as desired. Each of the torso straps 138 has a first portion 140 and a second portion 142. The first portion 140 has a first end fixedly joined to the torso section 134. A second end of the first portion 140 terminates in a first buckle half 144.

The second portion 142 of the torso straps 138 has a first end fixedly joined to the torso section 134. Each of the second portions 142 has a second buckle half 146 slidably disposed thereon. Each of the second buckle halves has a slip joint 148 coupled thereto in order that the position of the second buckle half 146 on the torso strap 138 may be adjusted.

The lower anchor 122 is designed to substantially encircle the trunk of the wearer proximate the pelvic region. The lower anchor 122 is comprised of a belt 150. The belt 150 is preferably formed of the same type of material as described above for forming the torso section 134. The belt 150 has a connector 152. The connector comprises one-half of a hook and loop type connector in conjunction with connector 154.

An optional, inflatable lumbar pillow is disposed on the inside surface of the belt 152. A lower torso section 158 extends between the upper anchor 120 and the lower anchor 122. The lower torso section 158 is stretchable in the vertical dimension, as depicted by arrows A. Lower torso section 158 provides for only minimal stretchability in the horizontal dimension.

In the embodiment depicted in FIGS. 10 and 11, four extender sets 124 extend between the upper anchor 120 and the lower anchor 122. There are two anterior extender sets 126, 128 and two posterior extender sets 130, 132.

The anterior extender sets 126, 128 each have two inflatable bladders 160. The upper portions of each of the bladders 160 is angled inward toward the center of the wearer's chest. The two posterior extender sets 130, 132 each have a single bladder 162. The two bladders 162 are angled slightly apart with the upper ends being further apart that the lower ends. It should be noted that each of the extender sets 126–132 may be comprised of a single bladder 160, 162, respectively, or multiple bladders 160, 162, as desired. The lower end of each of the bladders 160, 162 is affixed to the belt 150 and the upper end of each of the bladders 160, 162, is affixed to the torso section 134 of the upper anchor 120.

Referring to FIGS. 10a and 11, a pair of supportive shorts 104 is depicted. A generally triangular shape inflatable pelvic bladder 164 is disposed inside the front, anterior upper portion of the shorts 104. An adjustable pelvic belt 166 is disposed on the outside of the shorts 104. The belt 166 is disposed relatively low on the wearer with the posterior portion being proximate the wearer's sacrum and the anterior portion of the belt 166 crossing the pelvic bladder 164. A connector 168, preferably of the loop and hook type, is disposed in the anterior portion of the belt 166.

An alternative embodiment of the maternal support 100 is depicted in FIGS. 13–13b. In this embodiment, the maternal support 100 is integrated into a bodysuit 170. The bodysuit 170 is a bodice portion 172 and a waist portion 174. The bodice portion 172 acts as the upper anchor 120 of the maternal support 100 and the waist portion 174 acts as the lower anchor 122. Accordingly, the lower end of the anterior extender sets 126, 128 are affixed to the waist portion 174 of the bodysuit 170. The upper end of the anterior extender sets 126, 128 are affixed to the bodice portion 172 of the bodysuit 170. Likewise, the lower end of the posterior extender sets 130, 132 are affixed to the waist portion 174 of the bodysuit 170 and the upper end of the posterior extender sets 130, 132 are affixed to the bodice portion 172 of the bodysuit 170.

Referring to FIG. 14, the inflation system 176 for inflating the bladders 160, 162 of the extender sets 124 is depicted. The inflation system 176 includes a controller 178. The controller 178 may be worn on a separate belt by the wearer of the maternal support 100.

The controller 178 controls both the inflation and the deflation of the various inflatable devices of the maternal support 100. Accordingly, in order to obtain differential inflation anteriorly and posteriorly, the two anterior extender sets 126, 128 are inflatable by a common air line 182. In the depiction of FIG. 14, there are two posterior extender sets 130, 132. Additionally, there is a third, centrally disposed, posterior extender set 180. Each of the posterior extender sets 130, 132, and 180 are comprised of three individually inflatable bladders 162. All the bladders 162 of the posterior extender sets 130, 132, and 180 are inflatable by a common air line 184.

The optional lumbar pillow 156 is inflatable and deflatable by means of the controller 178 through air line 186. Further, the pelvic pillow 164 is inflatable and deflatable by means of the controller 178 acting through air line 188.

It should be noted that the controller 178 is coupled to a source of compressed air (not shown) by means of port 190.

Figure 15:
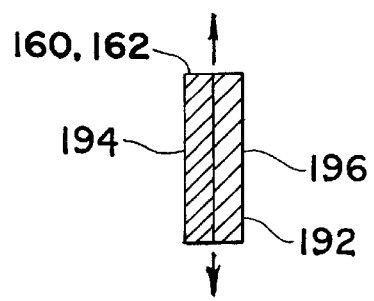
FIG. 15 is a side elevational view of a bi-woven uninflated bladder for an extender set.
Figure 15A:
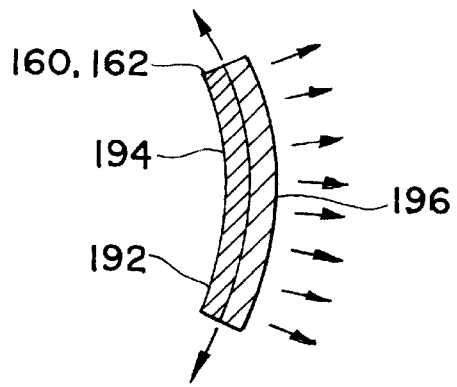
FIG. 15a is a side elevational view of the inflated bladder of FIG. 15.
Figure 16:
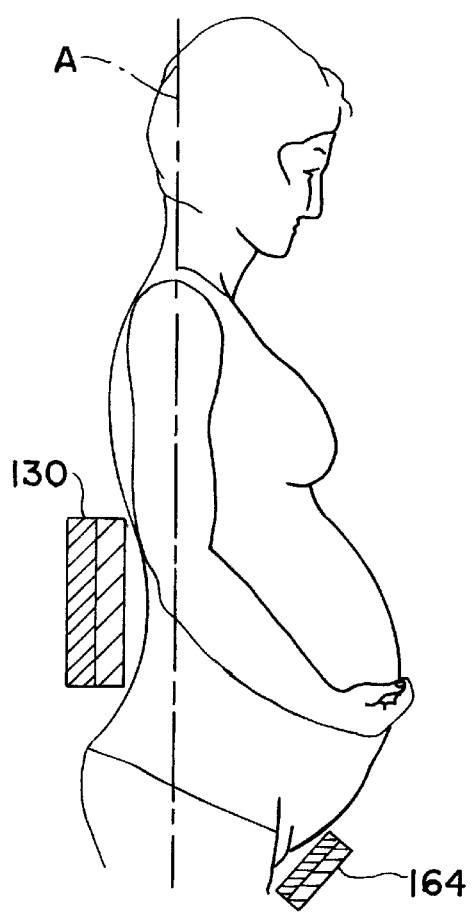
FIG. 16 is a side elevational view of a bi-woven uninflated bladder for an extender set and an uninflated pelvic bladder in relation to a wearing person.
Figure 16A:
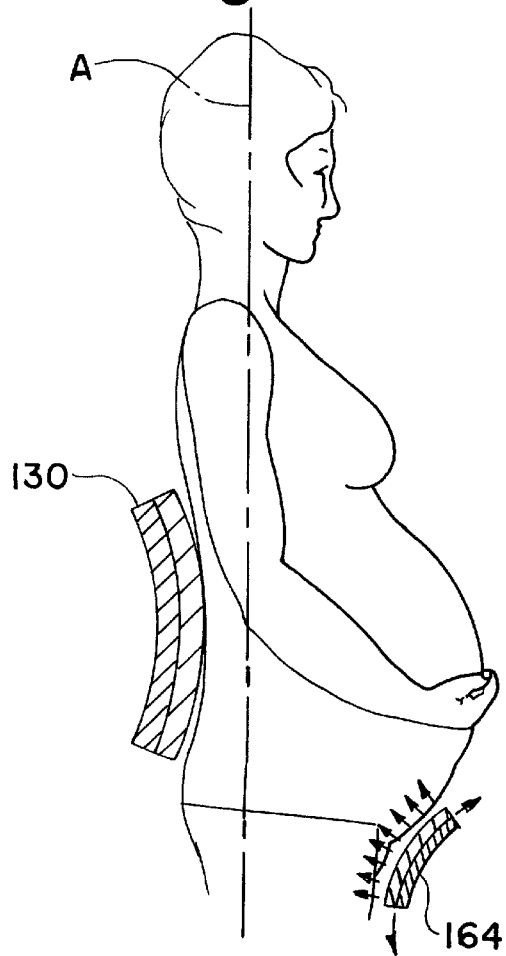
FIG. 16a is a side elevational view of the inflated bladder for an extender set and the pelvic bladder of FIG. 16.

FIGS. 15 and 15a are depictions of a typical bladder 160, 162 and the deflated state in FIG. 15 and the inflated state in FIG. 15a. The bladder 160, 162 has a sheath 192. The sheath 192 is bi-woven such that substantially half of the sheath 192 is comprised of heavy weaving 194 and the second half of the sheath 192 is comprised of light weaving 196. Upon inflation, as depicted in FIG. 15a, the bladder 160, 162 contained within the sheath 192 expands more in the region of light weaving 196 than in the region of heavy weaving 194. This uneven expansion causes the bladder 160, 162 to bend as depicted in FIG. 15. Such bending is useful in countering an undesired curve in the anatomy of the wearer, such as the exaggerated lumbar curve frequently evidenced in pregnant females. It should be noted that a bi-woven sheath may also be used in the construction of the lumbar pillow 156 and the pelvic bladder 164 in order to impart a distinct curvature thereto upon inflation. Referring to FIGS. 16 and 16a, FIG. 16a depicts exemplary bi-woven posterior extender set 130 and bi-woven pelvic bladder 164 in the uninflated condition. FIG. 16a depicts the posterior extender set 130 and the pelvic bladder 164 in the inflated condition. As noted, both the posterior extender set 130 and the pelvic bladder 164 assume a curvature with inflation. The curvature of the posterior extender set 130 and the pelvic bladder 164 tend to straighten the posture of the wearer as is evidenced by comparison of the posture of the wearer to the reference lines A of FIGS. 16 and 16a. The curvature of the posterior extender set 130 is exaggerated in FIG. 16a for illustrative purposes only. In reality, the posterior extender set 130 is constrained by the material of the vest 102 or bodice portion 172. The tendency to curve, however, results in the posterior extender set 130 acting to urge the wearer into a more erect posture, as depicted in FIG. 16a.

A further embodiment of the present invention is depicted in FIGS. 17a–25. The wrist support 200 has two major components: liner 202 and outer sheath 204. Referring specifically to FIGS. 17a, 17b, and 18b, the liner 202 is depicted in place on a human hand and lower arm. The liner 202 is preferably made of breathable bi-woven material. The bias of the weave of the liner 202 provides for relatively more expansion longitudinally as compared to expansion circumferentially. The longitudinal expandability of the liner 202 accommodates placing the carpal region of the wrist in tension upon inflation of the extender sets.

As depicted, the liner 202 has truncated digital apertures 214 in order to accommodate the thumb and fingers of the wearer projecting through the liner 202. The liner 202 has an extended gauntlet 216 that extends for a considerable distance up the distal end of the lower arm of the wearer. The gauntlet 216 has overlapping flaps 218 in order to secure the liner 202 to the arm of the wearer. The flaps 218 preferably have a coupling means such as loop and hook connectors. It should be noted that flaps 218 secure the liner 202 to the arm of the wearer away from the carpal region so that no undue circumferential pressure is applied to the carpal region.

A continuous bladder 206 is wound around the liner 202. The bladder 206 has an anterior transverse portion 208, depicted in FIG. 17a. The bladder 206 further has a posterior transverse portion 210 depicted in FIGS. 17b and 18b. The anterior transverse portion 208 and the posterior transverse portion 210 are fluidly coupled to a wrist portion 212. The wrist portion 212 extends from the anterior side of the liner 202, around at least a portion of the lower arm portion of the liner 202 to the posterior portion of the liner 202. Again, it should be noted that the wrist portion 212 of the bladder 206 avoids the carpal area so as to not unduly put pressure on the carpal area.

The portions of the liner 202 proximate the anterior transverse portion 208, the posterior transverse portion 210, and the wrist portion 212 of the bladder 206 comprise the anchors between which the bladder 206 under inflation applies tension to the carpal area. The portion of the liner 202 proximate the anterior transverse portion 208 and the portion of the liner 202 proximate the posterior transverse portion 210 comprise the upper anchor and the portion of the liner 202 proximate the wrist portion 212 comprises the lower anchor. The anterior transverse portion 208, the posterior transverse portion 210, and the wrist portion 212 are preferably bonded or molded to the liner 202 in order to establish the position of the anchors being spaced apart by the portion of the anatomy, the carpel area, to which the tension is to be applied.

As depicted in FIGS. 17b and 18b, a depending inflation tube 220 extends from the posterior transverse portion 210 of the bladder 206. The inflation tube 220 terminates in a coupler 222. The coupler 222 is readily mated to a cooperative coupler for fluid communication with the inflation bulb 228.

In an alternative embodiment, the bladder 206 can be bifurcated by seals 220. In such embodiment, the posterior transverse portion 210 of the bladder 206 is inflated by inflation bulb 218 and the anterior transverse portion 208 of the bladder 206 is inflated by a second inflation bulb 222, depicted in phantom in FIG. 18b. The presently described embodiment permits differential inflation of the bladder 206 and the anterior and posterior portions of the liner 202. Such differential inflation can control the amount of flexion of the hand with respect to the wrist of the wearer that is caused by the inflation of the bladder 206.

The outer sheath 204 is depicted in FIGS. 18a, 19a and 19b. The outer sheath 204 is useful to cover the exposed continuous bladder 206. The outer sheath 204 is substantially coterminous with the liner 202. Accordingly, outer sheath 204 has digit apertures 230 to accommodate the thumb and fingers of the wearer. A gauntlet 232 extends up the lower arm of the wearer. A wraparound strap 234 secures the gauntlet 232 to the lower arm of the wearer.

Figure 20:
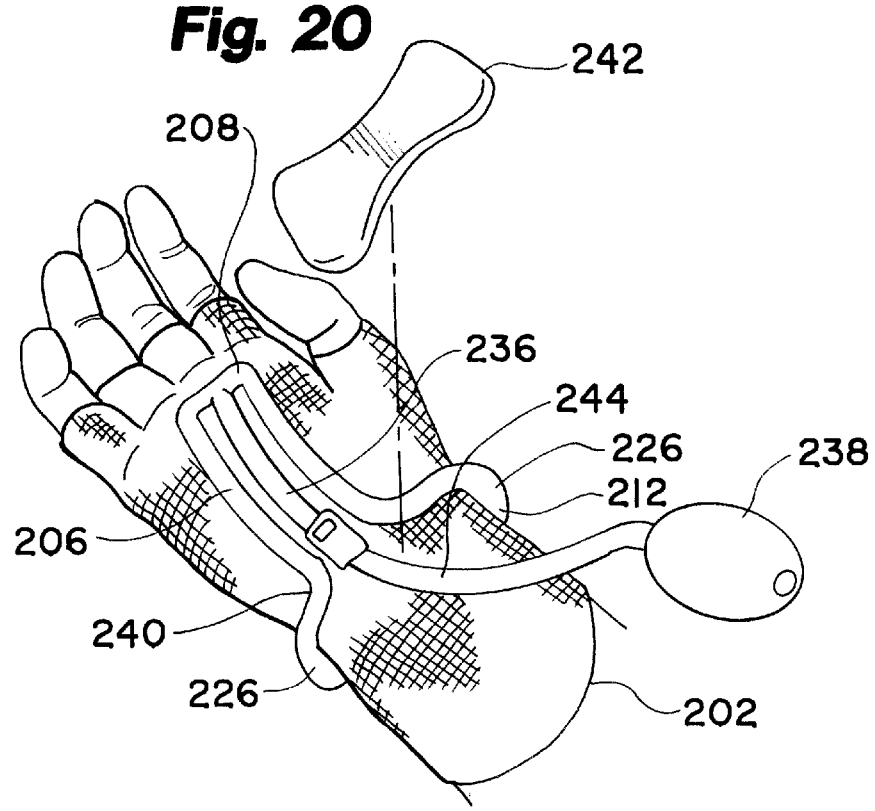
FIG. 20 is an anterior perspective view of the liner of the wrist support of the present invention with the cooling pad exploded away.
Figure 21:
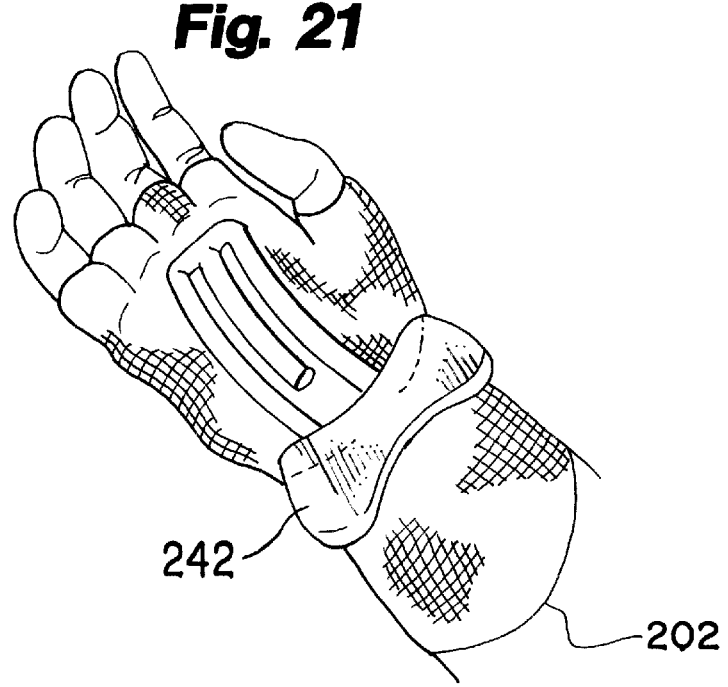
FIG. 21 is an anterior perspective view of the liner of the wrist support of the present invention with the cooling pad positioned over the carpal region of the wearer's wrist.

FIGS. 20 and 21 depict a second embodiment of the wrist support 200. As depicted in FIG. 20, the bladder 206 has seals 226 proximate the wrist portion 212 of the bladder 206. A depending inflation tube 236 is fluidly coupled to the anterior transverse portion 208 of the bladder 206. The inflation tube 236 may be coupled to an inflation bulb 238 by a quick-disconnect connector 240. The inflation bulb 238 of the present embodiment is utilized in conjunction with the inflation bulb 224 depicted in FIG. 18b to differentially inflate the anterior transverse portion 208 and the posterior transverse portion 210 of the bladder 206.

The embodiment of the wrist support 202 depicted in FIG. 20 is only of the liner 202. It is envisioned that an outer sheath 204, as previously described, is utilized with the depicted liner 202. A cooling pad 242 is designed to be placed over the carpal region 244. The cooling pad 242 is depicted in place in FIG. 21. Once in place, as depicted in FIG. 21, the outer sheath 204 is pulled over the liner 202 and the cooling pad 242. The cooling pad 242 is designed to be readily replaceable. A number of different, similar cooling pads 242 is provided with each of the wrist supports 200. In this manner cooling pads 242 that are not being used may be kept in a cool place, such as a household refrigerator, for replacement as the cooling pad 242 currently in use warms up.

Figure 22:
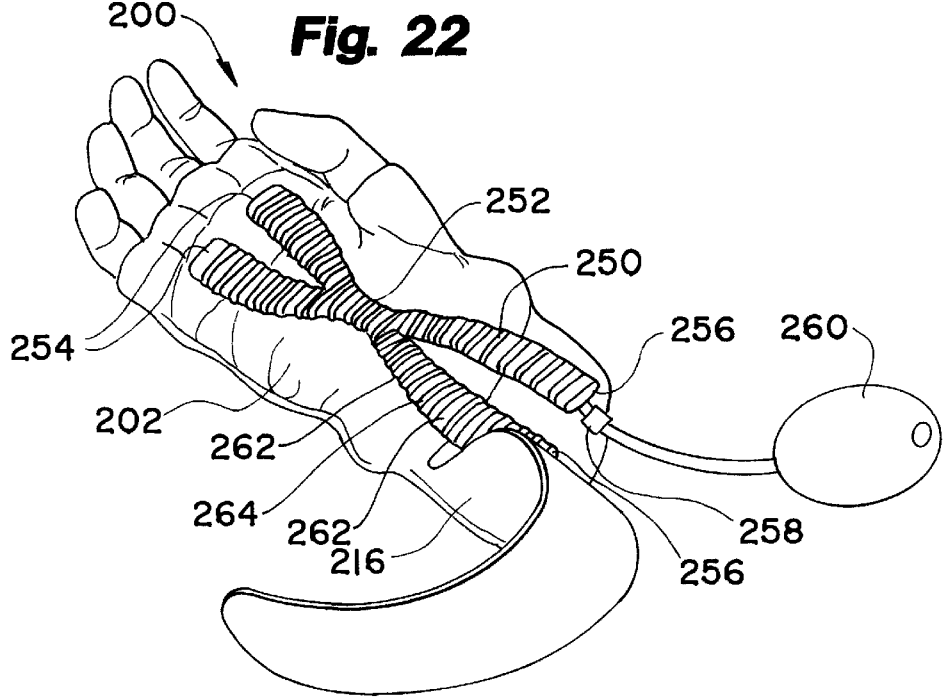
FIG. 22 is an anterior perspective view of the liner of the wrist support of the present invention with and alternative embodiment of the bladders of the extender sets.
Figure 23:
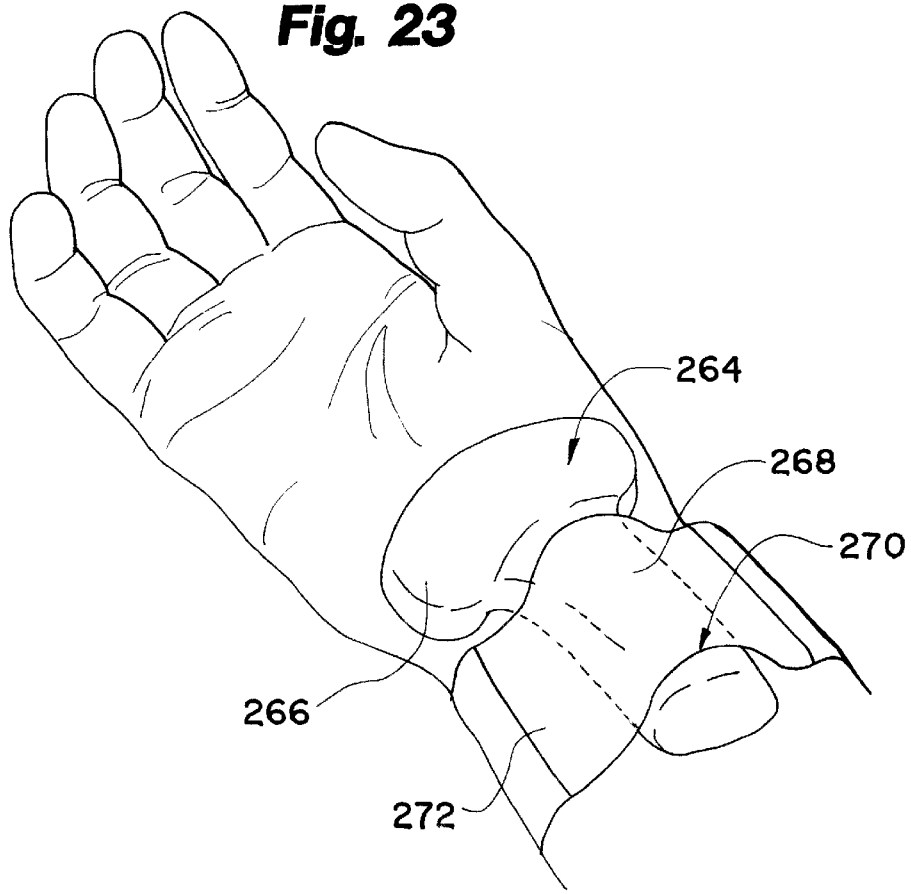
FIG. 23 is an anterior perspective view of the liner of the wrist support of the present invention with and alternative embodiment of the cooling pad.

Turning to FIG. 22, the liner 202 of a wrist support 200 is depicted on the hand of a wearer with the hand turned in the anterior position. The liner 202 of the embodiment depicted in FIG. 23 is substantially the same as previously described. The bladder 250 differs in construction to the previously described bladder 206, but is functionally the same as bladder 206. The bladder 250 is X-shaped having a common intersection 252 that fluidly couples all portions of the bladder 250. The upper ends 254 of the bladder 250 are fixedly joined by the liner 202, thereby providing the upper anchor necessary for applying the tension to the carpal region. The lower ends 256 are fixedly coupled to gauntlet 216 of the liner 202 to provide the lower anchor.

The bladder 250 is formed of individual segments 262 being preferably substantially rectangular in cross section. A flexible, expandable joint 264 is disposed between adjacent segments 262. The joint 264 and the adjacent segments 262 respond much as an accordion responsive to increased inflation of the bladder 250. Such increased inflation expands the joint 264 thereby spacing the adjacent segments 262 further apart. The bladder 250 has a quick-disconnect connector 258 coupled to an inflation bulb 260 for inflating the anterior bladder 250. A similar bladder 250 is affixed to the posterior side of the liner 202. Such similar bladder 250 is independently inflatable by an inflation bulb similar to the inflation bulb 260.

FIG. 23 depicts an alternative preferred embodiment of the cooling pad 264. In this embodiment, the cooling pad 264 has a bulbous head 266 disposed over the carpal region of the wearer's wrist. An extended shank 268 depends from the head 266. The shank 268 is loosely engaged in a retainer 270 of a wrist band 272. The retainer 270 forms a cavity between the retainer 270 and the wrist of the wearer. The wrist band 272 is preferably formed of a plastic material. In usage, the cooling pad 264 is disposed as depicted. The liner 202, as previously described, is then pulled over the cooling pad 264 and the wrist band 272.

Although the above description of preferred embodiments of the present invention clearly illustrates the concepts and practice of the invention, it will be recognized by one of skill in the art that the present invention may assume a plurality of embodiments. In recognition of this, the description provided above is illustrative only and not intruded as a limitation of what the applicant considers to be his invention, which invention is limited only by the metes and bounds of the claims set forth below.

I claim:

1. An ambulatory, wearable support to be worn by a person for applying an extending force to a portion of the human anatomy while being worn, the portion of the human anatomy having an anterior portion and an opposed posterior portion, comprising:

a first anchor member substantially encircling a first portion of the human anatomy;

a second anchor member spaced apart from the first anchor member, the portion of the human anatomy that is to be subjected to the extending force being disposed substantially between said first and second anchor members; and a plurality of extender sets, each of said sets having at least one selectively inflatable bladder and having a first end operably coupled to the first anchor member and a second end operably coupled to the second anchor member, the plurality of extender sets being spaced apart and disposed both anteriorly and posteriorly with respect to the portion of the human anatomy that is to be subjected to the extending force.

2. The ambulatory, wearable support of claim 1 wherein the least one selectively inflatable bladder in each extender set is responsive to an increase of gas pressure therein, the increase in gas pressure generating a force tending to extend the bladder along a central bladder axis and thereby acting to increase the space between the first and the second anchor members.

3. The ambulatory, wearable support of claim 2 wherein the least one selectively inflatable bladder in each extender set is operably, fluidly coupled to a source of compressed gas.

4. The ambulatory, wearable support of claim 3 wherein the gas pressure in the least one selectively inflatable bladder in each posteriorly disposed extender set is independently controllable with respect to the gas pressure in the least one selectively inflatable bladder in each anteriorly disposed extender set.

5. The ambulatory, wearable support of claim 1, the person having a skeletal system, wherein the inflation of the least one selectively inflatable bladder in each extender set acts on members of the skeletal system that are disposed substantially between said first and second anchor members.

6. The ambulatory, wearable support of claim 1 wherein an increase in inflation of the least one selectively inflatable bladder in each extender set acts generally to increase a spacing between members of the skeletal system that are disposed substantially between said first and second anchor members.

7. The ambulatory, wearable support of claim 1 wherein the extender sets are compliant for accommodating ordinary motions of the wearing person, said ordinary motions occurring between the first anchor member and the second anchor member.

8. The ambulatory, wearable support of claim 1 wherein the first anchor member substantially encircles the thorax of the wearing person and the second anchor member substantially encircles the pelvic region of the wearing person.

9. The ambulatory, wearable support of claim 8 further including a selectably inflatable lumbar pillow, the lumbar pillow being posteriorly disposed proximate the lumbar region of the wearing person.

10. The ambulatory, wearable support of claim 9 wherein increasing inflation of the posteriorly disposed extender sets tends to decrease the curvature of the spinal column of the wearing person in the lumbar region.

11. The ambulatory, wearable support of claim 8 further including a belt, the belt substantially encircling the wearing person proximate the sacrum, and a selectively inflatable pelvic bladder, the pelvic bladder being disposed interior to an anterior portion of the belt, increased inflation of the pelvic bladder tending to transfer weight bearing on the pelvic bladder to the belt, to be borne by the spinal column of the wearing person.

12. The ambulatory, wearable support of claim 1 wherein at least one inflatable bladder has a bias tending to induce a curve in the bladder upon inflation thereof.

13. The ambulatory, wearable support of claim 12 wherein the at least one biased bladder includes a bi-woven outer sheath.

14. The ambulatory, wearable support of claim 1 wherein at least one inflatable bladder is formed of a plurality of spaced apart segments, adjacent segments being joined by an expandable joint.

15. The ambulatory, wearable support of claim 14 wherein the expandable joint has an accordion-like structure.

16. The ambulatory, wearable support of claim 1 wherein the first anchor member substantially encircles a portion of the hand of the wearer and the second anchor member substantially encircles a portion of the lower arm of the wearer.

17. The ambulatory, wearable support of claim 16 wherein inflation of at least one extender set acts to place the carpal region of the wrist of the wearer in tension.

18. The ambulatory, wearable support of claim 17 wherein circumferential pressure is applied to the hand and lower arm of the wearer with the carpal region of the wrist being substantially free of circumferential pressure.

19. The ambulatory, wearable support of claim 16 further including a coolable pad selectively disposed proximate the carpal region on the anterior side of the wearer's wrist.

20. The ambulatory, wearable support of claim 16 further including a liner, the plurality of expander sets being affixed to the liner.

21. The ambulatory, wearable support of claim 20 wherein the liner is formed of a breathable material, the material having a bias being more longitudinally expandable than circumferentially expandable.

22. The ambulatory, wearable support of claim 21 wherein the liner material is bi-woven.

23. The ambulatory, wearable support of claim 16 having a single continuous bladder being anchored on an anterior hand portion of the liner, extending at least partially circumferentially around a gauntlet portion of the liner to a posterior hand portion of the liner.

* * * * *